United States Patent
Simmons

(10) Patent No.: US 8,612,010 B2
(45) Date of Patent: *Dec. 17, 2013

(54) UPPER EXTREMITY MUSCLE THERAPY SYSTEM

(75) Inventor: Randy Simmons, Ontario, CA (US)

(73) Assignee: Robotic Integrated Technology Development Corporation, Ontario, CA (US)

( * ) Notice: Subject to any disclaimer, the term of this patent is extended or adjusted under 35 U.S.C. 154(b) by 884 days.

This patent is subject to a terminal disclaimer.

(21) Appl. No.: 12/343,411

(22) Filed: Dec. 23, 2008

(65) Prior Publication Data

US 2010/0160986 A1   Jun. 24, 2010

(51) Int. Cl.
*A61N 1/04* (2006.01)

(52) U.S. Cl.
USPC ........................................................... 607/48

(58) Field of Classification Search
USPC .................................... 607/48; 128/892–894
See application file for complete search history.

(56) References Cited

U.S. PATENT DOCUMENTS

| | | | |
|---|---|---|---|
| 3,387,147 A | 6/1968 | Radwan | |
| 4,148,321 A | 4/1979 | Wyss et al. | |
| 4,177,819 A | 12/1979 | Kofsky et al. | |
| 4,323,060 A | 4/1982 | Pecheux | |
| 4,492,233 A | 1/1985 | Petrofsky et al. | |
| 4,509,509 A | 4/1985 | Bouvet et al. | |
| 4,520,827 A * | 6/1985 | Wright et al. | 607/48 |
| 4,653,479 A | 3/1987 | Maurer | |
| 4,724,842 A | 2/1988 | Charters | |
| 4,825,852 A | 5/1989 | Genovese et al. | |
| 4,838,272 A | 6/1989 | Lieber | |
| 4,947,836 A * | 8/1990 | Laenger et al. | 607/48 |
| 5,458,560 A | 10/1995 | Kaiser et al. | |
| 6,456,884 B1 | 9/2002 | Kenney | |
| 6,878,122 B2 | 4/2005 | Cordo | |
| 7,101,347 B2 | 9/2006 | Culhane et al. | |
| 7,252,644 B2 | 8/2007 | Dewald et al. | |
| 2004/0127954 A1* | 7/2004 | McDonald, III | 607/48 |
| 2004/0267331 A1 | 12/2004 | Koeneman et al. | |
| 2005/0015118 A1* | 1/2005 | Davis et al. | 607/49 |
| 2006/0167564 A1 | 7/2006 | Flaherty et al. | |

OTHER PUBLICATIONS

International Search Report and Written Opinion dated Mar. 11, 2010.

* cited by examiner

*Primary Examiner* — Eric D. Bertram
(74) *Attorney, Agent, or Firm* — James W. Hill; McDermott Will & Emery LLP

(57) ABSTRACT

Some embodiments of the present invention provide systems and methods for treating diminished muscle function. Some systems include an electrical member that delivers electrical energy to a hand region of a body that comprises a dysfunctional muscle; a joint motion assembly that couples to the body and provides, to a joint adjacent the dysfunctional muscle, a motion made up of a cycle of opposing joint movements; and a control unit that provides an operator of the system with control of a timing of electrical energy delivery and an amount of electrical energy delivered. Some systems time the electrical energy delivery to occur when the moving joint is near an inflection point and deliver electrical energy delivered in amounts effective to result in a depolarization of the dysfunctional muscle, a nerve in proximity of the joint, and/or a muscle of substantially normal function in proximity of the joint.

17 Claims, 9 Drawing Sheets

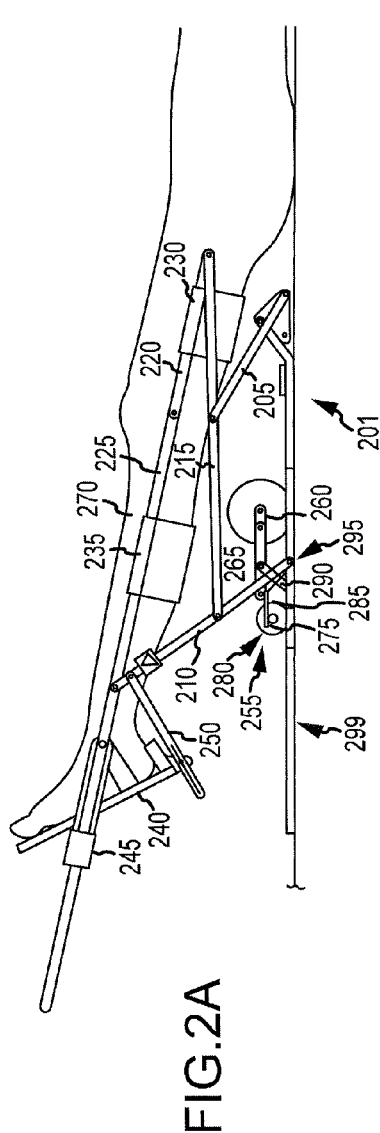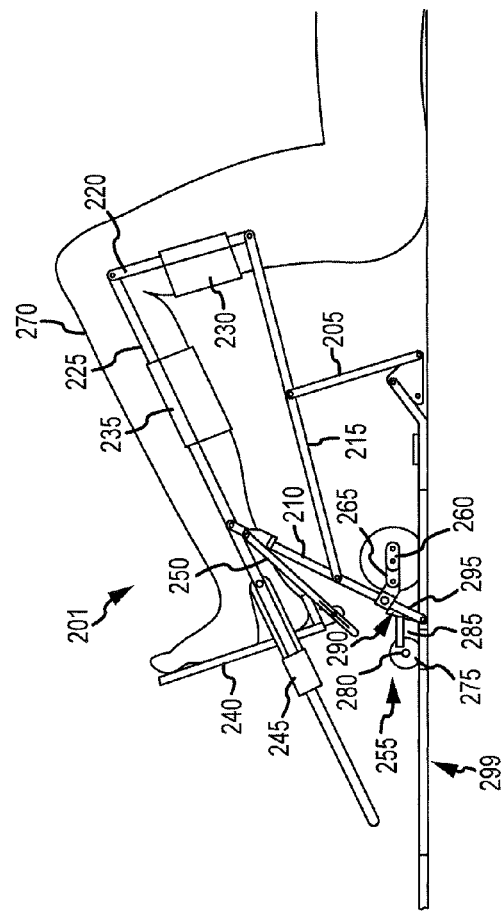
FIG.2A
FIG.2B

UPPER EXTREMITY MUSCLE THERAPY SYSTEM

FIELD OF THE INVENTION

The present invention provides muscle-therapy systems and methods for treating muscles of diminished capacity. Certain embodiments of systems and methods of the present invention are useful in promoting a return of function to muscles having diminished capacity due to spinal chord injury; a partially or completely severed nerve; neurodegenerative disease, such as ALS-Lou Gehrig's disease, Huntington's disease, multiple sclerosis, and Alzheimer's disease; stroke; transient ischemic attack; surgery; cancer, e.g., by a tumor compression of a nerve; arthritis; aging; athletic injury; etc.

BACKGROUND OF THE INVENTION

Spinal cord injury, neurodegenerative diseases, and stroke are high-incidence causes of nueromotor impairments that result in disability due to diminished muscle capacity and/or function. Other causes disabilities resulting from diminished muscle capacity include surgery, cancer, arthritis, and aging associated processes.

In the United States, approximately 10,000 people each year suffer spinal cord injury, and over 230,000 people live with disabilities due to diminished muscle function resulting from spinal cord injury. Diminished muscle function following a spinal cord injury can result in, for example, paralysis, insufficient muscle activity to achieve stepping, inadequate weight-bearing capacity, aberrant gait, uncoordinated movement, and balance deficit. Previously known rehabilitation methods used to treat such disabilities in individuals with spinal cord injury include stretching, strengthening, gait training, and the use of mechanical, electrical, and electromechanical devices. Although such methods often provide minor improvements in motor abilities in the first, post-injury year, such improvements typically plateau at negligible levels. No previously available rehabilitation method is reliably effective to overcome diminished muscle function resulting from spinal cord injury.

In the United States, neurodegenerative diseases such as amyotrophic lateral sclerosis (ALS), cerebral palsy, multiple sclerosis, Huntington's disease, Alzheimer's, etc. occur at high incidence, approximately in a range of from one to seven cases per 100,000 people. Diminished muscle function is a frequent symptom of such neurodegenerative diseases, and can result in impaired strength, impaired coordination, impaired mobility, impaired speech, and contracture. Previously known rehabilitation methods used to treat deficits in individuals with neurodegenerative disease include stretching, strengthening, gait training, and the use of mechanical, electrical, and electromechanical devices. But no previously available rehabilitation method is reliably effective to overcome diminished muscle function resulting from neurodegenerative disease.

In the United States, approximately 750,000 people each year have strokes, and over 4 million people live with a stroke induced disability. Diminished muscle function following stroke can develop as a result of motor neuron cell damage and/or death following a blood clot induced ischemic event. Diminished muscle function following stroke can also develop as a result of "learned nonuse," a phenomenon observed in stroke victims who, shortly after the stroke event, experience failure in attempting to move a body part partially or completely paralyzed, temporarily, by the stroke. The stroke victim learns how to compensate for this partial or complete paralysis by using body parts unaffected or less affected by the stroke to accomplish daily living activities. Such compensatory strategies become habit, and, eventually, the victim does not attempt to move the affected body part, even when it is neurologically possible to do so.

Previously known rehabilitation methods used to treat diminished muscle function in stroke victims include stretching, strengthening, gait training, and the use of mechanical, electrical, and electromechanical devices. But no previously available rehabilitation technique is reliably effective to restore muscle function lost or partially lost as a result of motor neuron cell lesion and/or death. No previously available rehabilitation technique is reliably effective to overcome diminished muscle function resulting from learned nonuse.

Neuromuscular stimulation devices have previously been developed and used in methods for rehabilitating people suffering from disabilities due to diminished muscle function. For instance, Radwan (U.S. Pat. No. 3,387,147) describes a muscle stimulating pulse generator which provides an electric pulse with a relatively high voltage-to-width ratio and a steep wavefront that stimulates muscle contraction. Wyss et al. (U.S. Pat. No. 4,148,321) discloses a muscular therapy device that makes muscles rhythmically contract and relax at a low frequency by modulating the frequency of an electric current delivered to the muscle. Kofskey et al. (U.S. Pat. No. 4,177,819) teaches an apparatus for stimulating a muscle for 2 to 20 seconds at 2 to 50 second intervals using a modulated electric current. The contents of each of U.S. Pat. No. 3,387,147; U.S. Pat. No. 4,148,321; and U.S. Pat. No. 4,177,819 are hereby incorporated by reference in their entireties.

Passive motion devices have previously been developed and used in methods for rehabilitating people suffering from disabilities due to diminished muscle function. For instance, Pecheux (U.S. Pat. No. 4,323,060) describes a motorized splint that supports and provides motion, to a knee joint of a human leg having diminished muscle function and Genovese et al. (U.S. Pat. No. 1,825,852) discloses a similar device programmable to provide a variety of sequences of passive motion for a variety of durations, such as continuous. Wright and Ober (U.S. Pat. No. 4,520,827) describes a continuous passive motion apparatus similar to the Pecheux and Genovese et al. The contents of each of U.S. Pat. No. 4,323,060; U.S. Pat. No. 1,825,852; and U.S. Pat. No. 4,520,827 are hereby incorporated by reference in their entireties.

People suffering from diminished muscle function due to spinal chord injury, neurodegenerative disease, stroke, surgery, cancer, arthritis, aging, etc. face relative inactivity and deterioration of muscles that would otherwise be active. Given that no previously known rehabilitation device or method is reliably effective in rehabilitating diminished muscle function, there is a need for rehabilitation methods and devices effective in restoring diminished muscle function.

SUMMARY OF THE INVENTION

Certain embodiments provide a system, for treating diminished muscle function, comprising: an electrical member that delivers electrical energy to a portion of a mammalian body, the body comprising a dysfunctional muscle; a joint motion assembly that couples to the body and provides a joint motion, in a cycle comprising opposing joint movements, to a joint of the body to which the dysfunctional muscle ordinarily provides motion; and a control unit, in communication with the member and the assembly, that controls (i) a timing of electrical energy delivery by the member and (ii) an amount of electrical energy delivered by the member; wherein the timing of electrical energy delivery is controlled to occur while both of the following occur simultaneously: (i) the joint is positioned near an inflection point between the opposing joint movements in the cycle, and (ii) motion is being provided to the joint by the joint motion assembly; and wherein the amount of electrical energy delivered is effective to result in a depolarization of at least one of the dysfunctional muscle and a nerve that innervates the dysfunctional muscle. As used herein, a "dysfunctional muscle" may have a diminished capacity because of disease or because of disrupted nerve conduction in an upper motor neuron or a lower motor neuron.

As the joint moves in one direction and then reverses direction in the cycle, the point at which it reverses direction is referred to herein as the "inflection point." When the joint is positioned near an inflection point between the opposing joint movements in the cycle, the joint is near its point of reversing motion in the cycle.

In certain embodiments, the depolarization results in a contraction of the dysfunctional muscle. In certain embodiments, the contraction results in a force on the joint that is antagonistic to the joint movement being provided by the joint motion assembly at the time of contraction. In certain embodiments, the contraction results in a force on the joint that is protagonistic to the joint movement being provided by the joint motion assembly at the time of contraction.

In certain embodiments, the member delivers the electrical energy when the joint is within about 20 degrees of the inflection point. In certain embodiments, the member delivers the electrical energy when the joint is within about 15 degrees of the inflection point. In certain embodiments, the member delivers the electrical energy when the joint is within about 10 degrees of the inflection point. In certain embodiments, the member delivers the electrical energy when the joint is within about 5 degrees of the inflection point.

In certain embodiments, the system further comprises a vibratory member, in communication with the control unit, that delivers vibratory energy to the portion of the body effective to result in activation of a mechanoreceptor in proximity to the joint.

Certain embodiments of providing a method, for treating diminished muscle function, comprising: contacting an electrical member, configured to deliver electrical energy, to a portion of a mammalian body, the body comprising a dysfunctional muscle; with a joint motion assembly, providing a joint motion, in a cycle comprising opposing joint movements, to a joint of the body to which the dysfunctional muscle ordinarily provides motion; and with the electrical member, delivering an amount of electrical energy to the portion of the body while both of the following occur simultaneously: (i) the joint is positioned near an inflection point between the opposing joint movements in the cycle, and (ii) the joint motion is being provided to the joint; wherein the amount of electrical energy delivered is effective to result in a depolarization of at least one of the dysfunctional muscle and a nerve that innervates the dysfunctional muscle.

In certain embodiments, the depolarization results in a contraction of the dysfunctional muscle. In certain embodiments, the contraction results in a force on the joint that is antagonistic to the joint movement being provided by the joint motion assembly at the time of contraction. In certain embodiments, the contraction results in a force on the joint that is protagonistic to the joint movement being provided by the joint motion assembly at the time of contraction. In certain embodiments, the delivery of electrical energy occurs when the joint is within about 20 degrees of the inflection point. In certain embodiments, the delivery of electrical energy occurs when the joint is within about 15 degrees of the inflection point. In certain embodiments, the delivery of electrical energy occurs when the joint is within about 10 degrees of the inflection point. In certain embodiments, the delivery of electrical energy occurs when the joint is within about 5 degrees of the inflection point.

In certain embodiments, the joint comprises an ankle joint, and wherein the opposing joint movements comprise a dorsiflexion and a plantarflexion of the ankle joint, and wherein the inflection point is within about 10 degrees of full plantarflexion.

In certain embodiments, the joint comprises an ankle tarsal joint, and wherein the opposing joint movements comprise an inversion and an eversion of the tarsal joint, and wherein the inflection point is within about 10 degrees of full inversion or eversion.

In certain embodiments, the joint comprises a subtalar joint of the ankle, and the opposing joint movements comprise an inversion and an eversion of the subtalar joint, and wherein the inflection point is within about 10 degrees of full inversion or eversion.

In certain embodiments, the joint comprises a knee joint, and wherein the opposing joint movements comprise a flexion and an extension of the knee joint, and wherein the inflection point is within about 10 degrees of full extension.

In certain embodiments, the joint comprises a hip joint, and wherein the opposing joint movements comprise a flexion and an extension of the hip joint, and wherein the inflection point is within about 10 degrees of full flexion or extension.

In certain embodiments, the joint comprises a hip joint, and wherein the opposing joint movements comprise an abduction and an adduction of the hip joint, and wherein the inflection point is within about 10 degrees of full abduction or adduction.

In certain embodiments, the joint comprises a hip joint, and wherein the opposing joint movements comprise an medial rotation and a lateral rotation of the hip joint, and wherein the inflection point is within about 10 degrees of full medial rotation or lateral rotation.

In certain embodiments, the joint comprises a shoulder joint, and wherein the opposing joint movements comprise a flexion and an extension of the shoulder joint, and wherein the inflection point is within about 10 degrees of full flexion or extension.

In certain embodiments, the joint comprises a shoulder joint, and wherein the opposing joint movements comprise a medial rotation and a lateral rotation of the shoulder joint, and wherein the inflection point is within about 10 degrees of full medial rotation or lateral rotation.

In certain embodiments, the joint comprises an elbow joint, and wherein the opposing joint movements comprise a flexion and an extension of the elbow joint, and wherein the inflection point is within about 10 degrees of full flexion or extension.

In certain embodiments, the joint comprises an elbow joint, and wherein the opposing joint movements comprise a pronation and a supination of the elbow joint, and wherein the inflection point is within about 10 degrees of full pronation or supination.

In certain embodiments, the joint comprises a wrist joint, and wherein the opposing joint movements comprise a flexion and an extension of the wrist joint, and wherein the inflection point is within about 10 degrees of full flexion or extension.

In certain embodiments, the joint comprises a wrist joint, and wherein the opposing joint movements comprise a supination and a pronation of the wrist joint, and wherein the inflection point is within about 10 degrees of full pronation or supination.

In certain embodiments, the joint comprises a wrist joint, and wherein the opposing joint movements comprise an ulnar deviation and a radial deviation of the wrist joint, and wherein the inflection point is within about 10 degrees of full ulnar deviation or radial deviation.

In certain embodiments, the vibratory member delivers the vibratory energy when the joint is within about 20 degrees of the inflection point. In certain embodiments, the vibratory member delivers the vibratory energy when the joint is within 15 degrees of the inflection point.

In certain embodiments, the vibratory member delivers the vibratory energy when the joint is within 10 degrees of the inflection point. In certain embodiments, the vibratory member delivers the vibratory energy when the joint is within 5 degrees of the inflection point.

In certain embodiments, a vibratory member, delivers vibratory energy to the portion of the body. In certain embodiments, the vibratory member delivers the vibratory energy when the joint is within about 20 degrees of the inflection point. In certain embodiments, the vibratory member delivers the vibratory energy when the joint is within about 15 degrees of the inflection point. In certain embodiments, the vibratory member delivers the vibratory energy when the joint is within about 10 degrees of the inflection point. In certain embodiments, the vibratory member delivers the vibratory energy when the joint is within about 5 degrees of the inflection point.

Certain embodiments provide a hand apparatus, for treating diminished muscle function, comprising: an electrical member that delivers electrical energy to a hand region comprising at least one of a digit, a hand, and a wrist, the hand region comprising a dysfunctional muscle; a hand joint motion assembly that couples to the hand region and provides a joint motion, in a cycle comprising opposing joint movements, to a joint of the hand, and the hand region to which the dysfunctional muscle ordinarily provides motion; and a control unit, in communication with the member and the assembly, that provides an operator of the system with control of: (i) a timing of electrical energy delivery by the member, and (ii) an amount of electrical energy delivered by the member; wherein the timing of electrical energy delivery is controlled to occur while both of the following occur simultaneously: (i) the joint is near an inflection point between opposing joint movements in the cycle, and (ii) motion is being provided to the joint by the joint motion assembly; and wherein the amount of electrical energy delivered is effective to result in a depolarization of at least one of the dysfunctional muscle and a nerve that innervates the dysfunctional muscle. As used herein, a "dysfunctional muscle" may have a diminished capacity because of disease or because of disrupted nerve conduction in an upper motor neuron or a lower motor neuron.

In certain embodiments, the depolarization results in a contraction of the dysfunctional muscle. In certain embodiments, the contraction results in a force on the joint that is antagonistic toward the joint movement being provided by the joint motion assembly at the time of contraction. In certain embodiments, the contraction results in a force on the joint that is protagonistic toward the joint motion being provided by the joint motion assembly at the time of contraction.

In certain embodiments, the member delivers the electrical energy when the joint is within about 20 degrees of the inflection point. In certain embodiments, the member delivers the electrical energy when the joint is within about 15 degrees of the inflection point. In certain embodiments, the member delivers the electrical energy when the joint is within about 10 degrees of the inflection point. In certain embodiments, the member delivers the electrical energy when the joint is within about 5 degrees of the inflection point.

In certain embodiments, a system comprises a vibratory member, in communication with the control unit, that delivers vibratory energy to at least one of the digit, the hand, and the wrist effective to result in activation of a mechanoreceptor in proximity to the joint. In certain embodiments, the vibratory member delivers the vibratory energy when the joint is within about 20 degrees of the inflection point. In certain embodiments, the vibratory member delivers the vibratory energy when the joint is within 15 degrees of the inflection point. In certain embodiments, the vibratory member delivers the vibratory energy when the joint is within 10 degrees of the inflection point. In certain embodiments, the vibratory member delivers the vibratory energy when the joint is within 5 degrees of the inflection point.

In certain embodiments, the joint comprises a wrist joint, and wherein the opposing joint movements comprise a flexion and an extension of the wrist joint, and wherein an inflection point joint angle for the flexion movement is in a range of from about 45 degrees to about 95 degrees, and wherein an inflection point joint angle for the extension movement is in a range of from about 45 degrees to about 95 degrees.

In certain embodiments, the joint comprises a wrist joint, and wherein the opposing joint movements comprise a supination and a pronation of the wrist joint, and wherein an inflection point joint angle for the supination movement is in a range of from about 45 degrees to about 90 degrees, and wherein an inflection point joint angle for the pronation movement is in a range of from about 45 degrees to about 90 degrees.

In certain embodiments, the joint comprises a wrist joint, and wherein the opposing joint movements comprise an ulnar deviation and a radial deviation of the wrist joint, and wherein an inflection point joint angle for the ulnar deviation movement is in a range of from about 20 degrees to about 40 degrees, and wherein an inflection point joint angle for the radial deviation movement is in a range of from about 10 degrees to about 25 degrees.

In certain embodiments, the joint comprises a finger metacarpophalangeal joint, and wherein the opposing joint movements comprise a flexion and an extension of the metacarpophalangeal joint, and wherein an inflection point joint angle for the flexion movement is in a range of from about 45 degrees to about 90 degrees, and wherein an inflection point joint angle for the extension movement is in a range of from about 0 degrees to about negative 10 degrees.

In certain embodiments, the joint comprises a proximal interphalangeal joint of a finger, and wherein the opposing joint movements comprise a flexion and an extension of the proximal interphalangeal joint, and wherein an inflection point for the flexion movement is in a range of from about 60 degrees to about 120 degrees, and wherein an inflection point joint angle for the extension movement is in a range of from about 5 degrees to about negative 10 degrees.

In certain embodiments, the joint comprises a distal interphalangeal joint of a finger, and wherein the opposing joint movements comprise a flexion and an extension of the distal interphalangeal joint, and wherein an inflection point for the flexion movement is in a range of from about 45 degrees to about 90 degrees, and wherein an inflection point joint angle for the extension movement is in a range of from about 5 degrees to about negative 10 degrees.

In certain embodiments, the joint comprises a metacarpophalangeal joint of a thumb, and wherein the opposing joint movements comprise a flexion and an extension of the metacarpophalangeal joint, and wherein an inflection point for the flexion movement is in a range of from about 35 degrees to about 70 degrees, and wherein an inflection point joint angle for the extension movement is in a range of from about 5 degrees to about negative 10 degrees.

In certain embodiments, the joint comprises an interphalangeal joint of a thumb, and wherein the opposing joint movements comprise a flexion and an extension of the interphalangeal joint, and wherein an inflection point for the flexion movement is in a range of from about 30 degrees to about 60 degrees, and wherein an inflection point joint angle for the extension movement is in a range of from about 5 degrees to about negative 10 degrees.

Certain embodiments provide a method, for treating diminished muscle function, comprising: contacting an electrical member, configured to deliver electrical energy, to a hand region comprising at least one of a digit, a hand, and a wrist, the hand region comprising a dysfunctional muscle; with a joint motion assembly, providing a joint motion, in a cycle comprising opposing joint movements, to a joint of the hand region to which the dysfunctional muscle ordinarily provides movement; and with the electrical member, delivering an amount of electrical energy to the hand region while both of the following occur simultaneously: (i) the joint is positioned near an inflection point of opposing joint movements, and (ii) the joint motion is being provided to the joint; wherein the amount of electrical energy delivered is effective to result in a depolarization, in the hand region, of at least one of the dysfunctional muscle and a nerve that innervates the dysfunctional muscle.

In certain embodiments, the depolarization results in a contraction the dysfunctional muscle. In certain embodiments, the contraction results in a force on the joint that is antagonistic toward the joint movement being provided by the joint motion assembly at the time of contraction. In certain embodiments, the contraction results in a force on the joint that is protagonistic toward the joint movement being provided by the joint motion assembly at the time of contraction.

In certain embodiments, the delivery of electrical energy occurs when the joint is within about 20 degrees of the inflection point. In certain embodiments, the delivery of electrical energy occurs when the joint is within 15 degrees of the inflection point. In certain embodiments, the delivery of electrical energy occurs when the joint is within 10 degrees of the inflection point. In certain embodiments, the delivery of electrical energy occurs when the joint is within 5 degrees of the inflection point.

In certain embodiments, a method comprises contacting at least one of the finger, the thumb, and the hand with a vibratory member, the vibratory member in communication with the control unit and configured to deliver vibratory energy to the least one of the finger, the thumb, and the hand; and with a control unit in communication with the vibratory member and the assembly, controlling, during the contacting of the vibratory member and the least one of the finger, the thumb, and the hand, vibratory energy delivery to occur: (i) when the joint is near an inflection point of opposing joint movements and while motion is provided to the joint by the joint motion assembly, and (ii) in an amount effective to result in a depolarization, in the hand region, of a Golgi body that is in proximity of the joint.

In certain embodiments, the vibratory member delivers the vibratory energy when the joint is within about 20 degrees of the inflection point. In certain embodiments, the vibratory member delivers the vibratory energy when the joint is within about 15 degrees of the inflection point. In certain embodiments, the vibratory member delivers the vibratory energy when the joint is within about 10 degrees of the inflection point. In certain embodiments, the vibratory member delivers the vibratory energy when the joint is within about 5 degrees of the inflection point.

In certain embodiments, the joint comprises a wrist joint, and wherein the opposing joint movements comprise a flexion and an extension of the wrist joint, and wherein an inflection point joint angle for the flexion movement is in a range of from about 45 degrees to about 95 degrees, and wherein an inflection point joint angle for the extension movement is in a range of from about 45 degrees to about 95 degrees.

In certain embodiments, the joint comprises a wrist joint, and wherein the opposing joint movements comprise a supination and a pronation of the wrist joint, and wherein an inflection point joint angle for the supination movement is in a range of from about 45 degrees to about 90 degrees, and wherein an inflection point joint angle for the pronation movement is in a range of from about 45 degrees to about 90 degrees.

In certain embodiments, the joint comprises a wrist joint, and wherein the opposing joint movements comprise an ulnar deviation and a radial deviation of the wrist joint, and wherein an inflection point joint angle for the ulnar deviation movement is in a range of from about 20 degrees to about 40 degrees, and wherein an inflection point joint angle for the radial deviation movement is in a range of from about 10 degrees to about 25 degrees.

In certain embodiments, the joint comprises a finger metacarpophalangeal joint, and wherein the opposing joint movements comprise a flexion and an extension of the metacarpophalangeal joint, and wherein an inflection point joint angle for the flexion movement is in a range of from about 45 degrees to about 90 degrees, and wherein an inflection point joint angle for the extension movement is in a range of from about 0 degrees to about negative 10 degrees.

In certain embodiments, the joint comprises a proximal interphalangeal joint of a finger, and wherein the opposing joint movements comprise a flexion and an extension of the proximal interphalangeal joint, and wherein an inflection point for the flexion movement is in a range of from about 60 degrees to about 120 degrees, and wherein an inflection point joint angle for the extension movement is in a range of from about 5 degrees to about negative 10 degrees.

In certain embodiments, the joint comprises a distal interphalangeal joint of a finger, and wherein the opposing joint movements comprise a flexion and an extension of the distal interphalangeal joint, and wherein an inflection point for the flexion movement is in a range of from about 45 degrees to about 90 degrees, and wherein an inflection point joint angle for the extension movement is in a range of from about 5 degrees to about negative 10 degrees.

In certain embodiments, the joint comprises a metacarpophalangeal joint of a thumb, and wherein the opposing joint movements comprise a flexion and an extension of the metacarpophalangeal joint, and wherein an inflection point for the flexion movement is in a range of from about 35 degrees to about 70 degrees, and wherein an inflection point joint angle for the extension movement is in a range of from about 5 degrees to about negative 10 degrees.

In certain embodiments, the joint comprises an interphalangeal joint of a thumb, and wherein the opposing joint movements comprise a flexion and an extension of the interphalangeal joint, and wherein an inflection point for the flexion movement is in a range of from about 30 degrees to about 60 degrees, and wherein an inflection point joint angle for the extension movement is in a range of from about 5 degrees to about negative 10 degrees.

BRIEF DESCRIPTION OF THE DRAWINGS

FIGS. 2A and 2B illustrate embodiments of a joint motion assembly configured to provide motion to a knee joint of a user of the system.

FIG. 6 illustrates an embodiment of a joint motion assembly configured to provide motion to a wrist joint of a user of the system.

DETAILED DESCRIPTION IF THE INVENTION

Certain embodiments of the present invention provide a muscle-therapy system, for treating a muscle of diminished function of a user of the system, comprising an electrical lead that delivers electrical energy to a region of a body of the user of the system in a proximity of a muscle of diminished function of the user; a passive joint motion assembly that couples to the body of the user of the system and thereby provides, to a joint of the body adjacent the muscle of diminished function, a joint motion that comprises a series of opposing joint movements; and a control unit that is in communication with the lead and the passive joint motion assembly so as to provide an operator of the system with control of a timing of electrical energy delivery by the lead, relative to the series of opposing joint movements, and an amount of electrical energy delivered by the lead.

In some embodiments, the system comprises a start switch, and the control unit is configured to start operation of the passive joint motion assembly in response to an input signal received from the start switch. In some embodiments, the system comprises a stop switch, and the control unit is configured to stop operation of the passive joint motion assembly in response to an input signal received from the stop switch, and the operator of the system can switch the start and stop switches. In some embodiments, the operator of the system can be a microprocessor, a healthcare provider, the user of the system, or a combination thereof.

In some embodiments, joint angles between inflection points of opposing joint movements provided by the joint motion assembly define a joint motion within a physiologic range.

In some embodiments, delivery of electrical energy by the lead is controlled to occur near, and not at, one or more inflection point(s) of joint movement, while the joint motion assembly provides motion to the joint; and the amount of electrical energy delivered by the lead is controlled to result in a depolarization of the muscle of diminished function, a nerve that is in a proximity of the joint, and/or a muscle of physiologic function that is in a proximity of the joint.

In certain embodiments, the system comprises a drive unit, coupled to the joint motion assembly, that provides movement to the joint motion assembly; and the drive unit can be in communication with the control unit. In some embodiments, the system comprises a joint motion assembly position sensor, in communication with the control unit, that provides signals indicative of the position of the joint motion assembly. In some embodiments, the control unit, in response to signals from the joint motion assembly position sensor, causes the drive unit to change a direction of the movement it provides to the joint motion assembly. In some embodiments, the control unit, in response to signals received from the joint motion assembly position sensor, causes the delivery of electrical energy by the lead.

Figure 1:
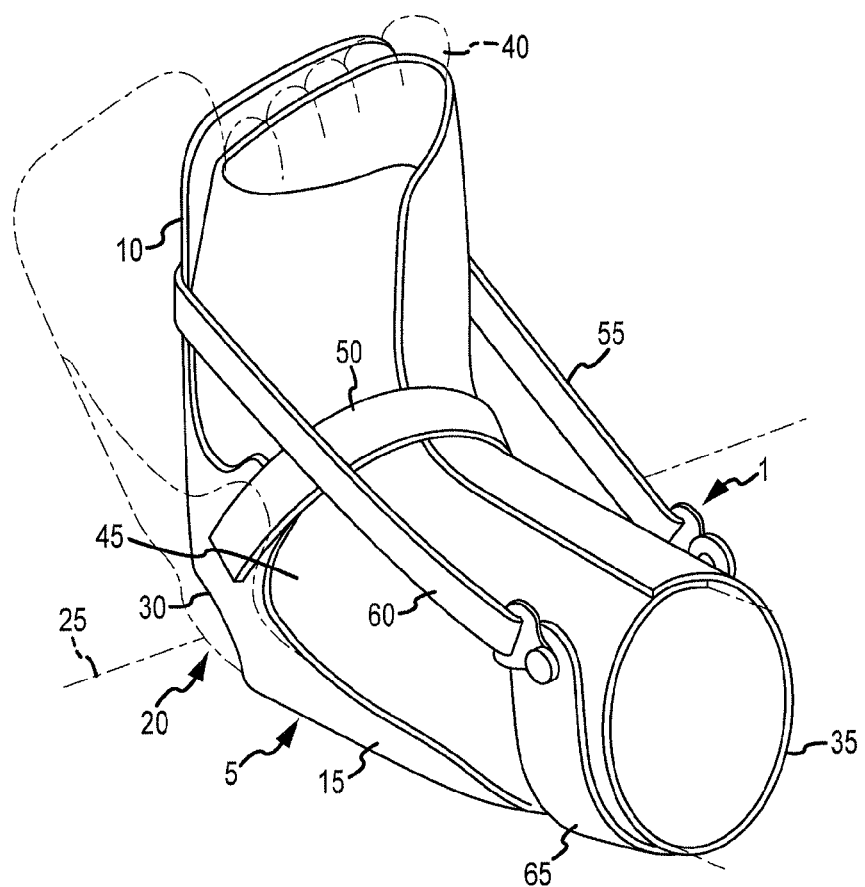
FIG. 1 illustrates an embodiment of a joint motion assembly configured to provide motion to an ankle joint of a user of the system.

In certain embodiments, the joint motion assembly is adapted to provide motion to an ankle joint of the user. Ankle joint motion assemblies are known in the art, and include assemblies such as the one illustrated in FIG. 1 1, which comprises a single piece or two piece carriage member 5 having sole region 10 and ankle region 15. In certain single piece embodiments, carriage member 5 comprises a flexible material, such as a plastic, and a cutout at heel region 20 to provide flexibility to carriage 5. In some embodiments, a transverse bend line is located along a transverse axis 25 through cutout 30. In certain two piece embodiments, an ankle joint motion assembly can comprise a hinge (not shown) that flexibly couples upper and lower regions of carriage 5 about transverse bend line 25. Ankle joint motion assembly 1 comprises padding 35 positioned between a foot, leg and ankle of the user, 40, 15, 45, respectively, and carriage member 5. Ankle joint motion assembly 1 comprises a detachable strap 50 for coupling the assembly 1 onto a foot 40 of the user. Ankle joint motion assembly 1 comprise adjustable right and left side straps 55 and 60, respectively, coupled to an upper end of ankle region 15 by a back-strap 65 and extend under sole region 10 for enabling alignment of foot 40. Joint motion assembly 1 comprises drive unit coupling members that couple upper and lower regions of carriage 5 to a drive unit that provides motion to assembly 1 and, thereby, movement to an ankle joint of the user of the system.

In certain embodiments, a joint motion assembly is adapted to provide motion to a knee joint of the user. Exemplary knee joint motion assemblies are known in the art, and include assemblies such as the one illustrated in FIG. 2 201, which comprises a pair of parallel rearward support links 205, a pair of parallel forward support links 210, a pair of drag links 215, a pair of femur support members 220, a pair of tibia support members 225, thigh support saddle 230, calf support saddle 235, foot support 240, connector 245, and connecting link 250. Links 205, 215, 220 and support members 220, 225 form a linkage that transmits drive power provided by drive unit 255 through crank 260 and link 265 to provide opposing knee joint 270 movements of extension (an exemplary inflection point joint angle of the extension is shown in FIG. 2A) and flexion (an exemplary inflection point joint angle of the flexion movement is shown in FIG. 2B).

In some embodiments, a joint motion assembly position sensor comprises a potentiometer that communicates, to the control unit, signals of increasing voltage proportional to increasing angles of components of the joint motion assembly. For example, joint motion assembly position sensor potentiometer 260, illustrated in FIGS. 2A and 2B, is connected to arm 290 links 280 and 285. The signal from potentiometer 275 can be an analog voltage signal, which can be converted to a digital signal, that is proportional to the angular position of arm 290. Forward support links 210 are pivotally connected to frame 299 by pivot shaft 295. Arm 290 is fixedly connected to pivot shaft 295, so that the angular position of arm 290 follows the angular position of forward support links 210. As a result, the joint motion assembly position signal provided by potentiometer 275 has a magnitude representative of the position of knee joint motion assembly 201 in its operating cycle of providing knee joint flexion and extension movements.

Figure 3A:
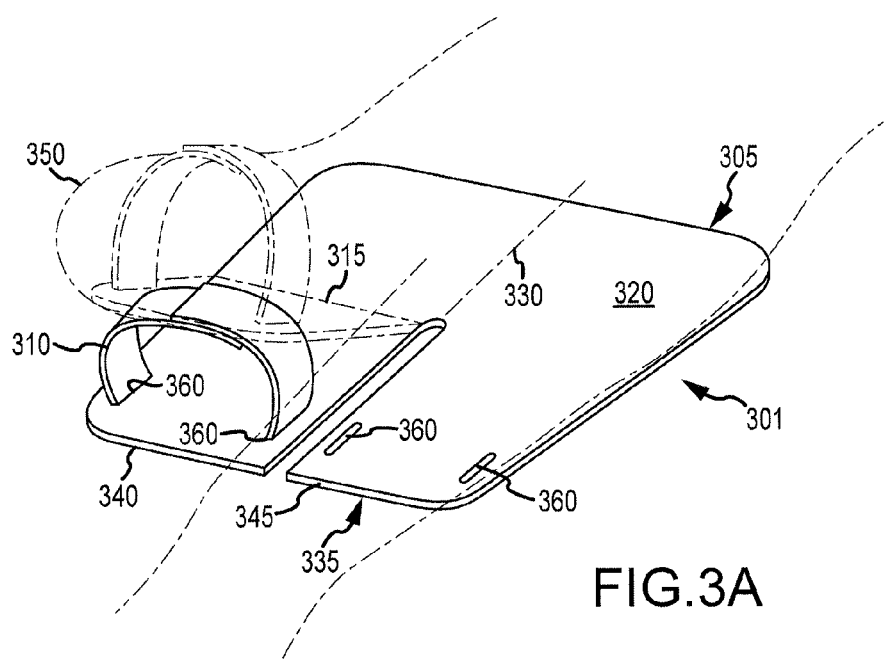
FIGS. 3A and 3B illustrate embodiments of a joint motion assembly configured to provide motion to a hip joint of a user of the system.
Figure 3B:
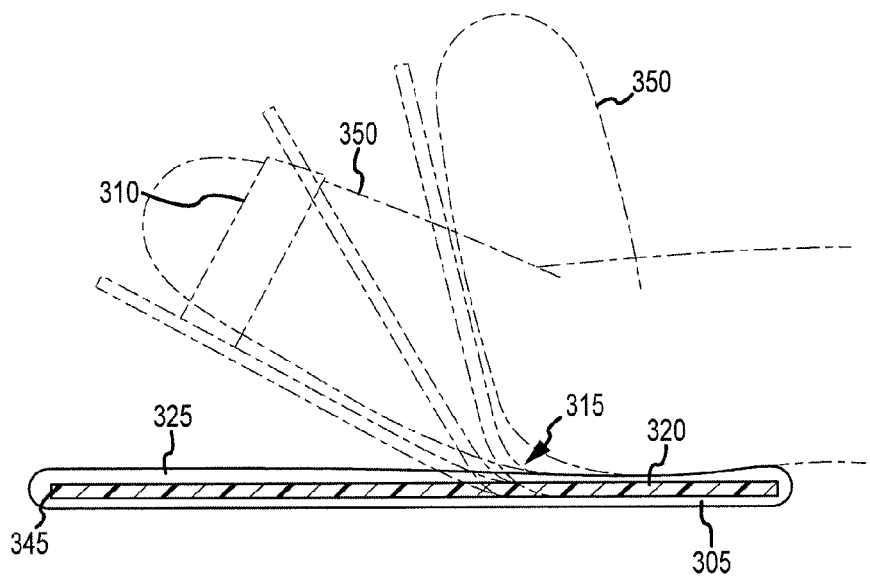

In certain embodiments, the joint motion assembly is adapted to provide motion to a hip joint of the user. Hip joint motion assemblies are known in the art, and include assemblies such as the one illustrated in FIG. 3 301, which comprises a single piece or two piece plate 305 and a detachable and adjustable leg attachment element 310. Plate 305 can be formed from flexible material, such as plastic, and configured to both support a hip region of the user and for bending about a transverse bend line 315. In certain two piece embodiments, plate 305 can be formed from an inflexible material, and comprise a hinge (not shown) that flexibly couples upper and lower regions, 320 and 325, respectively, of plate 305 about transverse bend line 315. In some embodiments, plate 305 comprises a slit that aligns with a thigh region of the user along a longitudinal axis 330, the slit defining side-by-side first and second thigh regions 335 and 340, respectively. Leg attachment element 310 is installed through slots 360 in either first or second thigh regions 335 or 340. In some embodiments, a hip joint motion assembly can comprise two leg attachment elements. Hip joint motion assembly 301 comprises a padded sleeve 325 (FIG. 3) installed over plate 305 to provide comfort to the user. When the user is lying on a surface 345, such as a massage table and plate 305, leg attachment element 310 is installed around a thigh region 350 of the user and tightened to couple thigh 350 against region 335 of assembly 301, upper plate region 320 being held down by the user's weight. Assembly 301 can comprise drive unit coupling members (not shown) that couple upper plate region and lower plate regions, 325 and 320, respectively, to a drive unit (not shown) that provides motion to a joint motion assembly and, thereby, movement to a hip joint of the user of the system.

Figure 4:
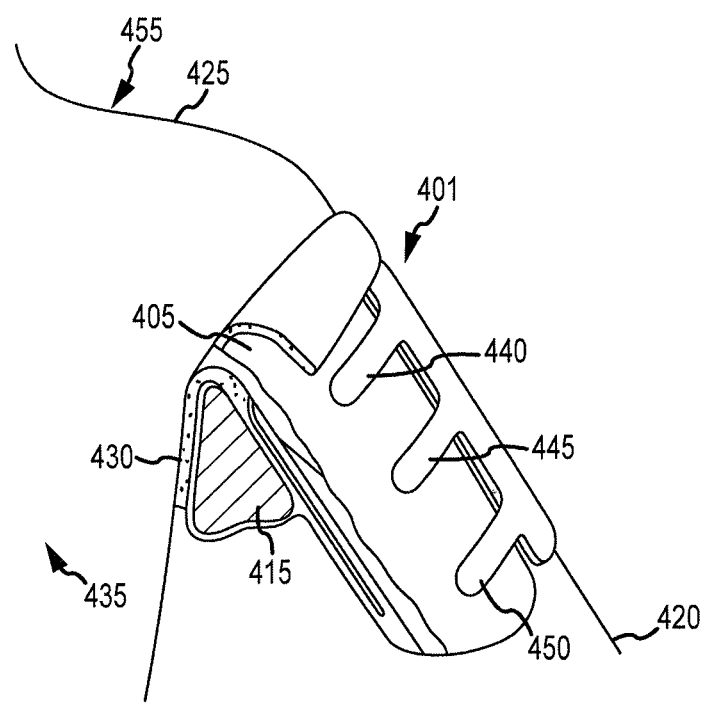
FIG. 4 illustrates an embodiment of a joint motion assembly configured to provide motion to a shoulder joint of a user of the system.

In certain embodiments, a joint motion assembly is adapted to provide motion to a shoulder joint of the user. Shoulder joint motion assemblies are known in the art, and include assemblies such as the one illustrated in FIG. 4 401, which comprises a flexible support element 405 having an internal recess or pocket 415 for receiving one or more flexible elements sized and configured (e.g., of increasingly denser or stiffer materials) to provide desired shoulder joint angles formed by the positioning of arm 420 relative to shoulder 425. Shoulder joint motion assembly 401 comprises a pad 430 that is positionable between support element 405 and arm 420 and thorax 435 of user 455 to provide comfort to user 455. Arm attachment elements 440, 445, 450 are configured to couple assembly 401 to arm 420 of user 455. In some embodiments, shoulder joint motion assembly 401 comprises drive unit coupling members (not shown) that couple the shoulder joint motion assembly to a drive unit that provides motion to the assembly and, thereby, movement to a shoulder joint of the user of the system.

In certain embodiments, the joint motion assembly is adapted to provide motion to an elbow joint of the user. Elbow joint motion assemblies are known in the art, and include assemblies such as the one illustrated in FIGS. 5A and 5B 501, which comprises an upper arm or humerus support 522, an elbow or flexion assembly 524, and a wrist or pronation/supination assembly 526. Upper arm or humerus support 522 comprises a lower or distal humerus cuff 528 and an upper or proximal humerus cuff 530. Cuff 530 is slidably mounted along cuff support 532.

Figure 5A:
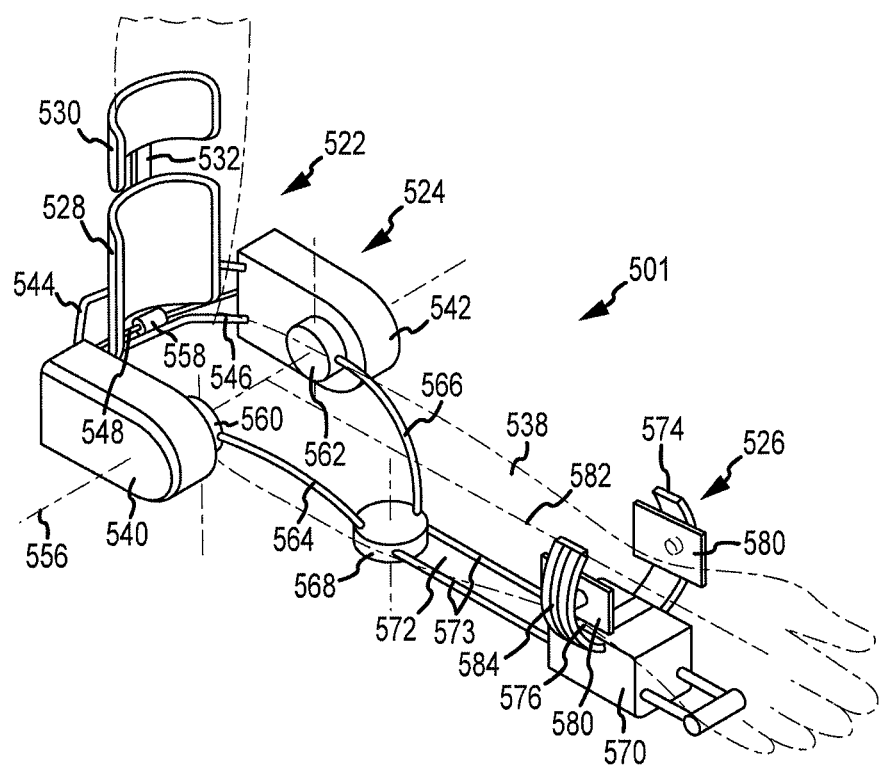
FIGS. 5A and 5B illustrate embodiments of a joint motion assembly configured to provide motion to an elbow joint of a user of the system.
Figure 5B:
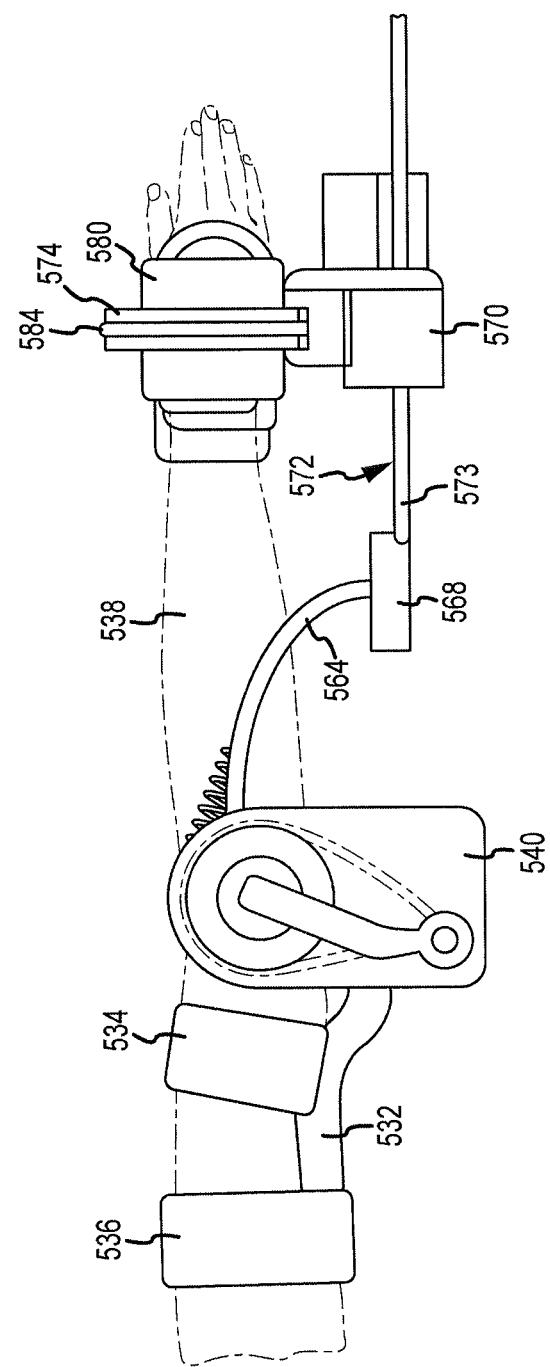

Lower cuff strap 534 (FIG. 5B) is coupled to lower humerus cuff 528 (FIG. 5A), and an upper cuff humerus strap 536 (FIG. 5B) is coupled to the proximal humerus cuff 530 (FIG. 5A). Straps 534 and 536 (FIG. 5A) can comprise fasteners, such as hook and loop fasteners, to allow for attachment and adjustment. A distance between the lower humerus cuff 528 and the proximal humerus cuff 530 can be adjusted to ensure that device 501 is securely attached to the patient shown in phantom 538.

Elbow assembly 524 comprises first and second elbow actuators 540 and 542, respectively, spaced apart top and bottom orthosis rods 544 and 546 and barrel nut assembly 548. First 540 and second 542 elbow actuators can be slidably coupled on side portions and top and bottom orthosis rods 544 and 546, respectively.

One of first 540 and second 542 elbow actuators can comprise a drive flexion elbow actuator and the other can comprise an idler elbow actuator. Elbow actuators 540 and 542 can each have a co-linear elbow axis of rotation 556. Barrel nut assembly 548 couples with threaded type connections at one end to first elbow actuator 540 and at the other end to second elbow actuator 542. Rotation of nut 558 in one direction causes elbow actuators 540 and 542 to move toward each other and rotation in the other direction causes them to move away from each other. As elbow actuators 540 and 542 move relative to each other the elbow axis of rotation 556 remains co-linear.

The elbow assembly 524 can be configured to be adjustable in order to accommodate patients with different sized elbows and different position of the elbow axis or rotation relative to humerus support 522. First and second elbow actuators 540 and 542 can slidably move along top and bottom orthosis rods 544 and 546, away from each back portion, resulting in a decrease of a distance of elbow axis 556 relative to humerus support 522 and accompanied by a proportionately increased distance between the first and second elbow actuators 540 and 542. So, by adjusting the barrel nut assembly 548, the patient or health care worker uses one adjustment to accommodate differences in upper arm circumferences and differences in position of the arm elbow anatomic axis relative to the posterior surface of the arm.

First and second actuators 540 and 542 comprise first and second rotating shafts 560 and 562, respectively. Rotating shafts 560 and 562 can rotate in a concentric fashion with elbow axis 556. First and second drive stays 564 and 566, respectively, are connected at one end to first and second rotating shafts 560 and 562. At the other end, first and second drive stays 564 and 566 can be are connected to valgus pivot 568. Pronation-supination assembly 526 can be coupled to valgus pivot 568.

Pronation-supination assembly 526 includes pronation-supination housing 570, housing shaft 572, ring assembly 574, and ulna clamping device 576. Housing shaft 572 can comprise a pair of parallel rods 573. Pronation-supination housing 570 can be slidably coupled to parallel rods 573 so as to be movable along the rods. Rods 573 can comprise a bent portion at the distal end, which limits movement of the pronation-supination housing 570. At the other end rods 573 can be coupled to valgus pivot 568.

Ring assembly 574 comprises a variable ulna clamp 576 on the inside thereof. Padding and soft materials 580 can be coupled to screw clamps for comfort. Screw clamps 576 can be adjustable to compensate for variations in the size of a patient's distal radius and ulna as well as centering the patient's limb along pronation-supination axis 582. The center of ring assembly 574 can be concentric with pronation-supination axis 582. The soft materials 580 of pronation-supination assembly 526 can be secured to the ulna clamping mechanism 576, and soft materials 580 provide a comfortable patient interface and drive point for the distal radius and ulna. Soft materials 580 can accommodate a range of wrist flexion and deviation positions when secured to the pronation-supination drive.

Ring assembly 574 can be slidably mounted in pronation-supination housing 570. An external belt 584 can move the ring in a rotational fashion relative to pronation-supination housing 570. Pronation-supination housing 570 can include a pronation-supination actuator that drives belt 584, which in turn drives ring assembly 574. Ring assembly 574 is sized to allow the distal portion of the forearm of the patient to be positioned and secured in the center of the ring assembly 574. Pronation-supination axis 582 can be arranged such that it is concentric with the anatomic axis of the patient's forearm. Pronation-supination housing 570 can be slidably mounted in a radial fashion relative to the elbow axis. Ulna clamp device 576 can be configured to secure the patient's distal radius and ulna so as to effectively transfer flexion and pronation-supination from the humerus to the forearm. Ulna clamp device 576 can be secured at the patient's distal radius and ulna wrist bone, or at any position along the ulna.

In certain embodiments, the joint motion assembly is adapted to provide motion to a wrist joint of the user. Exemplary passive wrist joint motion assemblies are known in the art, and include the assembly illustrated in FIG. 6 601, which comprises main housing unit 622, having upper portion 624 and lower portion 626, which can be configured to form an enclosure that can house a motion producing device and other internal components of the continuous passive motion assembly. Yoke member 628 comprises two spaced-apart arms 630, and can be rigidly supported by and extends outwardly from upper portion 624 of main housing unit 622. Yoke member 628 can be integrally formed with upper portion 624 of main housing unit 622. Yoke member 628 can also constitute a separate article, which can be formed of a different material and coupled to main housing unit 622. A plurality of stiffening ribs 632 can be provided on each of arms 630 in the area between each of arms 630 and upper portion 624 of main housing unit 622 to provide enhanced structural support and strength to arms 630.

At outward (i.e., remote from main housing unit 622) ends of spaced-apart arms 630, coaxially arranged first pivotal connection parts 634 (which together comprise a first pivotal connection) can be configured to pivotally connect outer ends of each of spaced-apart arms 630 to first link mechanism 636. As shown in FIG. 6, first pivotal connection parts 634 can be configured as ball joints that accommodate relative angular movement between yoke 628 and first link mechanism 636 about axes perpendicular to pivot axis of first pivotal connection parts 634.

First link mechanism 636 can be generally V-shaped when viewed from the side or longitudinal cross-section. First link mechanism 636 can comprise first bifurcated leg portion 638 and second bifurcated leg portion 640, coupled to one another so as to form an acute angle therebetween in the vicinity of an apex or apex portion. Accordingly, the first link mechanism can be a rigid, unitary torque/force-transmitting member. The term "link mechanism" as used herein encompasses both a unitary torque/force-transmitting member made from a single piece and a torque/force-transmitting arrangement made from a plurality of pieces which function in unison.

As shown in FIG. 6, bifurcated leg portion 638 terminates in a pair of free ends 644 at a position remote from an apex portion. Free ends 644 together constitute an end portion of first bifurcated leg portion 638, and can be connected to an end of yoke member 628 (constituted by the outer ends of the spaced-apart arms 630) remote from main housing unit 622 at first pivotal connection. Hand supporting assembly 646 is mounted on first link mechanism 636 at a position near apex portion 642.

Main housing unit 622, yoke member 628, first pivotal connection parts 634, and hand-supporting assembly 646 can be arranged so that, when main housing unit 622 is secured to a forearm of a user, a carpal joint of the user's wrist is in general alignment with first pivotal connection and the user's hand is substantially horizontally supported by hand-supporting assembly 646. In securing a forearm of the user to main housing unit 622, upper portion 624 can be configured with a plurality of longitudinally arranged securing elements 648 (which may take the form of removable rods). The forearm of the user is secured to a forearm splint 648a which includes two sets of two parallel channels 648b each for slidably receiving a securing element 648. Straps or attaching portions of soft materials (not shown) is adaptable so as to be fed beneath securing elements 648 and wrapped around the user's forearm, thereby securing the user's forearm to top portion 624 of main housing unit 622 without the need for splint 648a. The user's hand can rest on hand-supporting assembly 646. In certain embodiments, a strap (not shown) can be used to secure the user's hand to the hand-supporting assembly.

Other passive joint motion assemblies are known in the art and can be used in practicing certain embodiments of the present invention, such as those described in U.S. Pat. Nos. 5,458,560, 6,456,884, and 7,101,347, the entire contents of which are hereby incorporated by reference in their entireties.

Figure 7A:
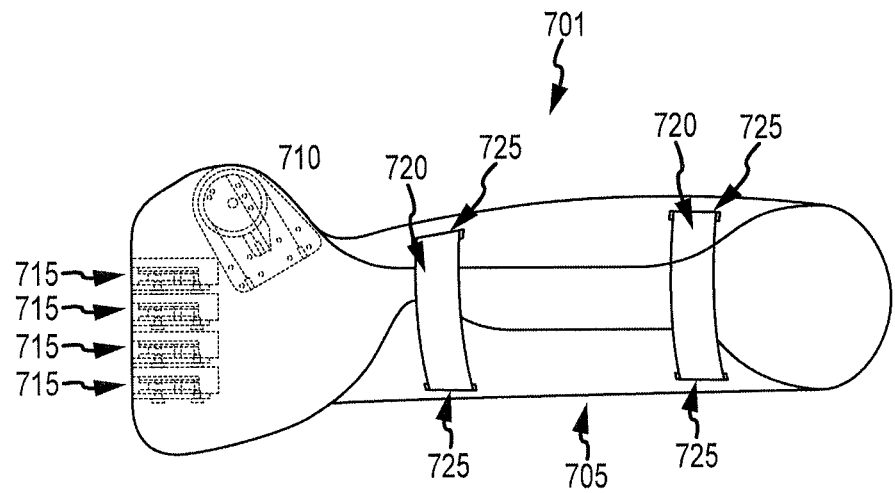
FIGS. 7A and 7B illustrate embodiments of a joint motion assembly, and parts thereof, configured to provide motion to joints of a thumb, a finger, a wrist, a hand, or a combination thereof, of a user of the system.

In certain embodiments, the passive joint motion assembly is adapted to provide motion to a hand of the user. As used herein, a "hand joint motion" assembly refers to a joint motion assembly adapted to provide motion to at least one of a finger joint, a thumb joint, and a wrist joint of the user. Exemplary hand joint motion assemblies of the present invention include assembly 701 illustrated in FIG. 7. Hand joint motion assembly 701 comprises forearm support member 705 and finger/thumb pivot assemblies 715. Forearm support member 705 and finger/thumb pivot assemblies 715 can comprise an inflexible material, such as metal, plastic, carbon fiber, wood, or combinations thereof. In certain embodiments, forearm support member 705 and finger/thumb pivot assemblies 715 can comprise structures that, together, confer a glove-like shape to the hand joint motion assembly 701.

Hand joint motion assembly 701 comprises user coupling elements 720, and user coupling elements 720 can be secured to the frame by securing members, such as slots 725. Other suitable securing members include Velcro, buttons, and hook and loop type securing members (not shown). User coupling elements 720 are configured to adjustably and reversibly couple a forearm region of the user's body to hand joint motion assembly 701. User coupling elements 720 can comprise fasteners, such as Velcro, buttons, and a hook and loop fasteners.

Forearm support member 705, finger/thumb pivot assembly 715, or a combination thereof, can be configured to adjustably conform to a physiologic curve of a forearm, a wrist, a hand, a thumb, a finger, or a combination thereof, of a normal human. Forearm support member 705, thumb/finger pivot assembly 715, or a combination thereof, can also be configured to adjustably conform to a non-physiologic curve of a forearm, wrist, hand, thumb, finger, or combination thereof, of the user.

Figure 7B:
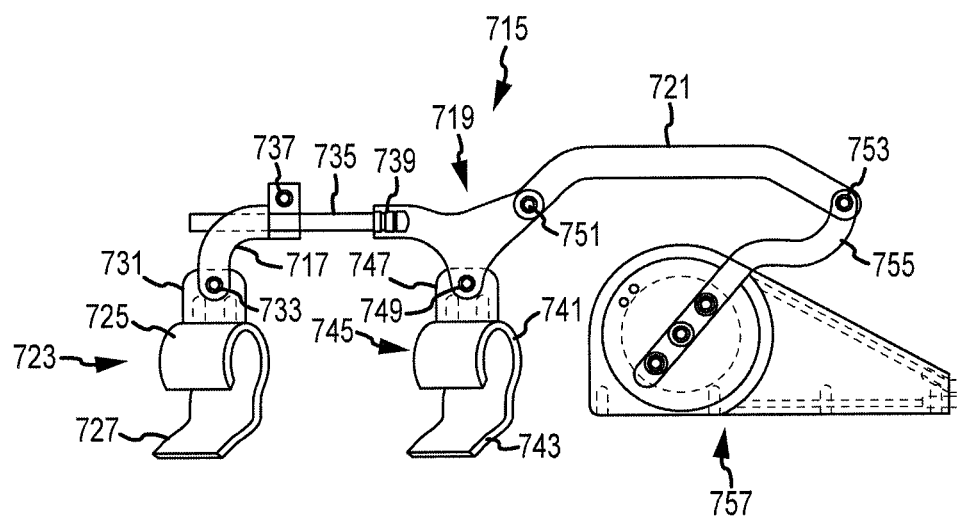

FIG. 7B illustrates a finger/thumb pivot assembly 715, of hand joint motion assembly 701, comprises rear finger pivot 717, center finger pivot member 719, and drive member coupling element 721. Rear finger pivot member 717 couples to rear finger housing member 723, which is configured to reversibly couple to a distal portion of a finger of a user of the system such as a distal interphalangeal segment and a middle phalanx segment. Rear finger housing member 723 comprises rear finger support frame 725, which is configured to reversibly receive and support the distal portion of the user's finger while providing motion to a joint in proximity to the distal portion of the user's finger, such as an interphalangeal joint, including distal and proximal interphalangeal joints. Rear finger support frame 725 can comprise an inflexible material, such as metal, wood, plastic, and carbon fiber. Rear finger support frame 725 comprises rear finger coupling element 727, which can be, e.g., a strap, a string, or a belt that reversibly couples the distal portion of the finger to rear finger housing member 723 and, thereby, to finger pivot assembly 715. Rear finger coupling element 727 can comprise a fastener, such as Velcro, buttons, and hook and loop type fastener members.

Rear finger housing member 723 comprises rear finger securing element 731, which comprises tap 733. Finger pivot 717 also comprises tap 733. Tap 733 is configured to adjustably receive a pin or a bolt type fastener (not shown), which provides a pivotally adjustable and reversibly fixed connection between rear finger housing member 723 and rear finger pivot member 717.

Finger pivot assembly 715 also comprises rear finger arm 735, which is configured to provide a slidably adjustable and reversibly fixed connection to rear finger pivot 717 by way of tap 737, which is configured to adjustably receive a pin or a bolt type fastener (not shown). Rear finger arm 735 is also adjustably and reversibly coupled to center finger pivot member 719 by way of a threaded portion, which is rotatably received by threaded tap 739 in center finger pivot member 719.

Center finger housing member 745 comprises center finger securing element 747, which comprises tap 749. Center finger pivot member 719 also comprises tap 749. Tap 749 is configured to adjustably receive a pin or a bolt type fastener (not shown), which provides a pivotally adjustable and reversibly fixed connection between center finger housing member 745 and center finger pivot 719.

Center finger pivot member 719 couples to center finger housing member 741, which is configured to reversibly couple to a proximal portion of a finger of a user of the system such as a middle phalanx segment and a proximal phalanx segment. Center finger housing member 745 comprises rear finger support frame 741, which is configured to reversibly receive and support the proximal portion of the user's finger while providing motion to a joint in a proximity to the proximal portion of the user's finger, such as an interphalangeal joint, e.g., a proximal interphalangeal joint and a metacarpophalangeal joint. Center finger support frame 741 can comprise an inflexible material, such as metal, wood, plastic, and carbon fiber as well as center finger support frame 743, a strap or belt that reversibly couples the proximal portion of the user's finger to center finger housing member 741 and, thereby, finger pivot assembly 715. Center finger coupling element 743 can comprise a fastening member, such as Velcro, buttons, and hook and loop type fastener members.

Finger pivot assembly 715 further comprises drive coupling element 721, which comprises bore 751. Center finger pivot also comprises bore 751. Bore 751 is configured to adjustably receive a pin or a bolt type fastener (not shown), which provides a pivotally adjustable and reversibly fixed connection between center finger pivot 719 drive coupling element 721.

Drive coupling element 721 and drive arm 755 further comprise bore 753, which is configured to adjustably receive a pin or a bolt type fastener (not shown) that provides a pivotally adjustable and reversibly fixed connection between drive coupling element 721 and a drive arm 755. Drive arm 755 is fixedly attached to pulley type drive unit 757 and thereby provides motion to the finger pivot assembly.

In certain embodiments, the hand motion assembly is coupled to a user of the system such that the wrist is set back with an angle in a range of from about 10 degrees to about 20 degrees, positioning that facilitates natural functional grip. In such embodiments, finger movement initiated by the pulleys can have an arch in a range of from about 150 degrees to about 190 degrees. Also in such embodiments, every other finger housing can be offset in a range of from about 0.5 inches to about 1.0 inches, providing clearance for the fingers while performing the flexion movement. In certain embodiments, the finger housing can comprise an adjustable split clamp for adjusting to the user's finger length.

As used herein, the term "finger" includes all digits of the human hand, including, e.g., a thumb digit and first, second, third, and fourth digits, sometimes referred to as pointer finger, index finger, ring finger, and pinkie fingers.

Figure 8:
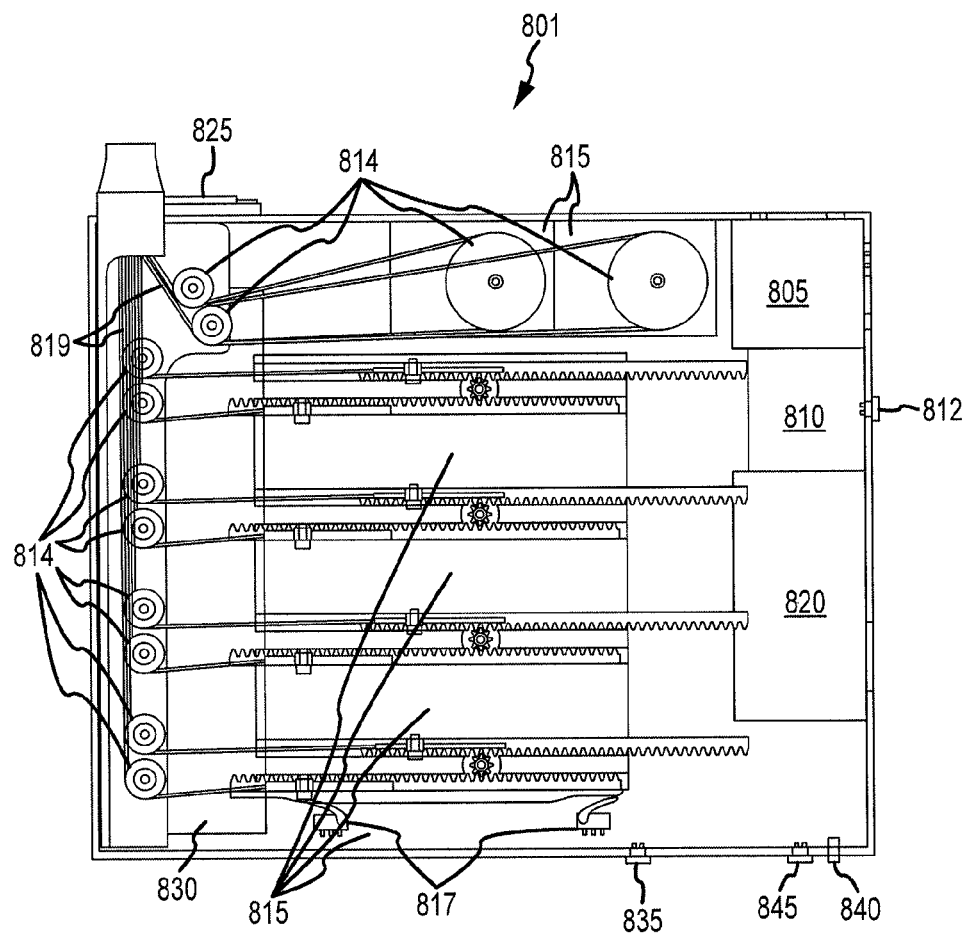
FIG. 8 illustrates an embodiment of a control box of the present invention.
Figure 9:
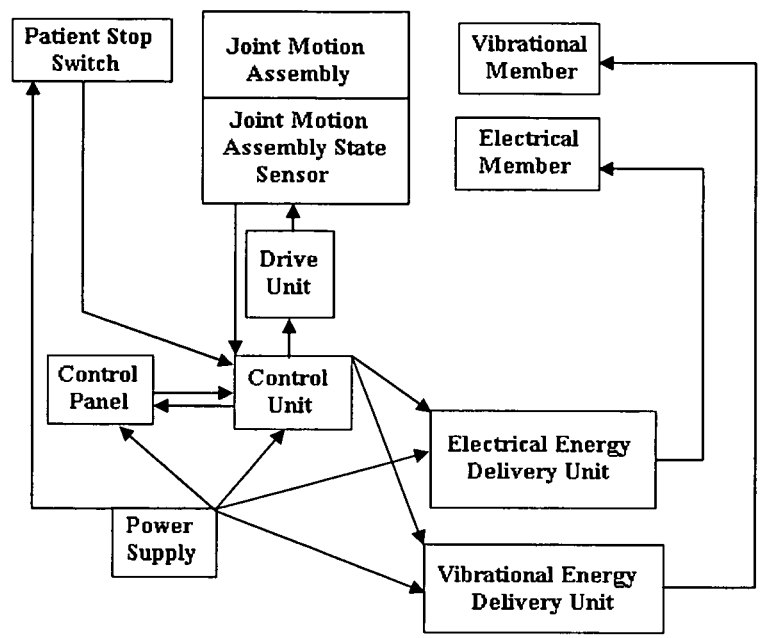
FIG. 9 illustrates a diagram of communications between components of an embodiment of a muscle therapy system.

FIG. 8 illustrates an embodiment of a control box useful in certain embodiments of the present invention. Control box 801 comprises electrical energy delivery unit 805, a vibratory energy delivery unit 810 that comprises vibrator switch 812, six stepper motors 815 that provide motion to a joint motion assembly, drive member linking cables 819 that operatively couple, through pulleys 814, a motion of stepper motor 815 to a joint motion assembly (not shown). Sensor 817 is configured to produce signals indicative of a temperature of the control box 801 and direction, speed, and position of stepper motor 815. Control box 801 comprises BS2 control board 820 that comprises a micro-processor (not shown), fan 825, and power supply 830. Power supply 830 is configured to provide power to electrical energy delivery unit 805, vibratory energy delivery unit 810, stepper motors 815, BS2 control board 820, and fan 825. Control box 801 further comprises 110 alternating current socket 835, USB port 840, and fire wire port 845.

In certain embodiments, a control box microprocessor is in communication with sensor 817 of stepper motor 815, electrical energy delivery unit 805, and vibratory energy delivery unit 810. In certain embodiments, a control box microprocessor can be programmed to coordinate a motion provided to a joint of a user of the system, by a joint motion assembly, with the provision of electrical energy by the electrical energy delivery unit 805 to a neuron, a muscle, or combination thereof of the user of the system. In certain embodiments, a control box microprocessor can be programmed to coordinate a motion provided to a joint of the user of the system, by a joint motion assembly, with the provision of vibratory energy by vibratory energy delivery unit 810 to a muscle, Golgi body or other mechanorecptor, tendon, or combination thereof of the user of the system. In certain embodiments, a control box microprocessor can be programmed to save information about the user's use of the system, e.g., speed of joint motion, range of joint motion, timing and amount of electrical and/or vibratory energy obtained from sensor 817, stepper motors 815, electrical energy delivery unit 805, vibratory energy delivery unit 810, and/or a joint motion assembly while a user uses the system.

In certain embodiments, a control box microprocessor is in communication with sensor 817 and fan 825. In certain embodiments, a control box microprocessor can be programmed to activate fan 825 in response to signals from the temperature sensor indicative of a threshold temperature in the control box.

In certain embodiments, chains (not shown) can be used instead of or together with drive member linking cables 819. In certain embodiments, sprockets (not shown) can be used instead of or together with pulleys 814.

In certain embodiments, a joint motion system can comprise at least two of an ankle joint motion assembly, a knee joint motion assembly, a hip joint motion assembly, a shoulder joint motion assembly, an elbow joint motion assembly, a wrist joint motion assembly, and a hand joint motion assembly.

In certain embodiments, a control box determines the inflection point joint angles of flexion and extension movements provided by a passive joint motion assembly based upon a comparison of the magnitude of joint motion assembly position sensor signals with predetermined values of inflection point joint angles of flexion and extension. When each predetermined joint angle inflection point value is reached by the joint motion assemble, the control unit changes the direction of a drive unit to change the direction of movement of the joint of a user moved by the joint motion assembly.

In certain embodiments, a joint motion assembly is configured with voice recognition capability so that the joint motion assembly provides a preprogrammed movement to a joint in response to a spoken command. For instance, a hand joint motion assembly, configured as a glove, can be configured to open or close a user's hand in response to spoken commands such as "open" and "close," respectively. Along these lines, a glove style hand joint motion assembly can be configured to bring digits of the hand, e.g. the index and thumb, together in response to a spoken command such as "pinch," or to raise the index finger in response to a spoken command such as "point." Voice recognition programs are known and can be provided by, e.g., a control box comprising a microphone or other sound-detecting device coupled to microprocessor means having voice recognition capabilities.

In certain embodiments, a joint motion assembly can comprise vibratory elements positioned to provide vibratory stimulation to a muscle, a nerve, a tendon, a Golgi body or other mechanoreceptor, or combinations thereof that is in a proximity of a joint adjacent to a dysfunctional muscle of the user of the system being treated. In certain embodiments, vibratory elements can provide vibratory stimulation while a joint of the user is being moved by the joint motion assembly or while the joint is stationary. In certain embodiments, a vibratory element can provide vibratory stimulation while the joint of the user is being moved by the joint motion assembly in a repeated series of movements comprising a cycle; and the vibratory stimulation can be provided continuously throughout the cycle or intermittently throughout the cycle. In certain embodiments, the vibratory stimulation can be provided near joint movement inflection points. As used here, the term "near joint movements inflection points" includes joint angles about 1°, about 2°, about 3°, about 4°, about 5°, about 6°, about 7°, about 8°, about 90°, about 10°, about 11°, about 12°, about 13°, about 14°, about 15°, about 16°, about 17°, about 18°, about 19°, about 20°, about 21°, about 22°, about 23°, about 24°, about 25°, about 30°, about 35°, and about 40° in of an inflection point of a joint motion. In certain embodiments, the vibratory stimulation can be provided in an amount effective to result in a depolarization of a neuron, a Golgi organ or other mechanoreceptor, or a combination thereof.

In certain embodiments, a joint motion assembly can comprise electrical elements positioned to provide electrical stimulation to a muscle, a nerve, a tendon, a Golgi organ or other mechanoreceptor, or combination thereof that is in a proximity of a joint adjacent to a dysfunctional muscle of a user of the system being treated. In certain embodiments, electrical elements can provide electrical stimulation while a joint of the user is being moved by the joint motion assembly or while the joint is stationary. In certain embodiments, the electrical elements can provide electrical stimulation while the joint of the user is being moved by the joint motion assembly in a repeated series of movements comprising a cycle; and the electrical stimulation can be provided near joint movement inflection points.

In certain embodiments, the electrical stimulation can be provided in an amount effective to result in a depolarization of a motor neuron, a sensory neuron, a Golgi organ or other mechanoreceptor, a muscle, or a combination thereof. In certain embodiments, the depolarization of a muscle resulting from the electrical stimulation results in a contraction of the muscle. In certain embodiments, the contraction of the muscle assists a joint motion assembly providing motion to a joint of a user of the system (i.e., a contraction of the muscle is agonistic to the joint motion provided by the joint motion assembly). In certain embodiments, the contraction of the muscle opposes a joint motion assembly provides motion to a joint of a user of the system (i.e., a contraction of the muscle is antagonistic to the joint motion provided by the joint motion assembly). In certain embodiments, electrical members can comprise transdermal stimulating pads. In certain embodiments, a transdermal electrical pad that provides positive electrical energy can be positioned at an intrinsic muscle of the user that is adjacent to a joint moved by the joint motion assembly and another transdermal electrical pad that provides negative electrical stimulation energy can be positioned above a point of injury to the user that has resulted in a muscle dysfunction in the user, such as on the back of the user's neck, such that, when the positive transdermal electrical pad and the negative transdermal electrical pad provide electrical energy to a user, a residual stimulation is forced through the nervous system in past the point of injury. In certain embodiments, the vibratory stimulation and the electrical stimulation can be provided in a coordinated manner or in a non-coordinated manner. For instance, vibratory and electrical stimulation can be provided simultaneously or in a series in which vibratory and/or electrical stimulation are provided when a joint, moved by a joint motion assembly, achieves one or more particular joint angles.

In certain embodiments, one or more vibration elements, such as coin style vibrators, can be configured and positioned to deliver stimulatory vibration energy to at least one of a dysfunctional muscle and a tendon of a dysfunctional muscle. In certain embodiments, one or more vibration elements, such as coin style vibrators, can be configured and positioned to deliver stimulatory vibration energy to at least one of a muscle adjacent to a dysfunctional muscle and a tendon adjacent to a dysfunctional muscle. In some embodiments, a vibration element can be built into a joint motion assembly.

In certain embodiments, stimulatory neuromuscular electrical energy can be applied to a user of the muscle therapy system by at least two electrical leads positioned and configured for transcutaneous delivery of the stimulatory electrical energy or positioned and configured for intramuscular delivery of the stimulatory electrical energy. The stimulatory electrical energy can be delivered in an amount effective to result in at least one of a contraction of a muscle, a depolarization of at least a portion of a membrane of a muscle cell, and a depolarization of at least portion of a membrane of a nerve cell. In some embodiments, a negative electrical lead can be placed adjacent to a joint moved by a joint motion assembly and a positive electrical lead can be positioned at a site at the core of the body of user. In some embodiments, a negative electrical lead that can be positioned adjacent to and above a site of injury on an extremity of the body of the user and a positive electrical lead can be positioned at the distal end of the extremity.

In certain embodiments, magnets can be used in combination with a joint motion assembly and at least one of stimulatory vibrational energy and stimulatory neuromuscular electrical energy.

In some embodiments, an inflection point joint angle of a dorsiflexion movement provided to an ankle joint by a joint motion assembly is about 10 degrees, about 7 degrees, about 5 degrees, or about 2 degrees. In some embodiments, an inflection point joint angle of a dorsiflexion movement provided to an ankle joint by a joint motion assembly is about 30 degrees, about 25 degrees, about 20 degrees, about 15 degrees, about 10 degrees, about 5 degrees, or about 2 degrees. In some embodiments, an inflection point joint angle of a dorsiflexion movement or a plantarflexion movement provided to an ankle joint by a joint motion assembly corresponds to an angle measured by a goniometer in which the fulcrum of the goniometer is aligned with the lateral malleolus of the user, the stationary arm of the goniometer is in line with the midline of the lower leg of the user, using the head of the fibula for reference, and the moving arm of the goniometer is parallel to the fifth metatarsal of the user.

In some embodiments, an inflection point joint angle of an inversion movement of a tarsal joint provided by a joint motion assembly is about 45 degrees, about 40 degrees, about 35 degrees, about 30 degrees, about 25 degrees, about 20 degrees, about 15 degrees, about 10 degrees, about 5 degrees, or about 2 degrees. In some embodiments, an inflection point joint angle of an eversion movement of a tarsal joint by a joint motion assembly is about 25 degrees, about 20 degrees, about 15 degrees, about 10 degrees, about 5 degrees, or about 2 degrees. In some embodiments, an inflection point joint angle of an inversion movement or an eversion movement of a tarsal joint provided by a joint motion assembly corresponds to an angle measured by a goniometer in which the fulcrum of the goniometer is positioned between the two malleoli of the user, the stationary arm of the goniometer is in line with the midline of the tibia of the user, and the moving arm of the goniometer is in line with the second metatarsal of the user.

In some embodiments, an inflection point joint angle of an inversion movement of a subtalar joint provided by a joint motion assembly is 20 degrees, about 15 degrees, about 10 degrees, about 5 degrees, or about 2 degrees. In some embodiments, an inflection point joint angle of an eversion movement of a subtalar joint by a joint motion assembly is about 15 degrees, about 10 degrees, about 5 degrees, or about 2 degrees. In some embodiments, an inflection point joint angle of an inversion movement or an eversion movement of a subtarsal joint provided by a joint motion assembly corresponds to an angle measured by a goniometer in which the fulcrum of the goniometer is positioned between the two malleoli of the user, the stationary arm of the goniometer is in line with the midline of the leg of the user, and the moving arm of the goniometer is in line with the midline of the calcaneus of the user.

In some embodiments, an inflection point joint angle of a flexion movement provided to a knee joint by a joint motion assembly is about 150 degrees, about 140 degrees, about 130 degrees, about 120 degrees, about 110 degrees, about 100 degrees, about 90 degrees, about 80 degrees, about 70 degrees, about 60 degrees, about 50 degrees, about 40 degrees, about 30 degrees, about 20 degrees, about 10 degrees, or about 5 degrees. In some embodiments, an inflection point joint angle of an extension movement provided to a knee joint by a joint motion assembly is about negative 10 degrees, about negative 5 degrees, about 0 degrees, about 5 degrees, about 10 degrees, about 20 degrees, about 30 degrees, about 40 degrees, and about 50 degrees. In some embodiments, an inflection point joint angle of a flexion movement or an extension movement provided to an ankle joint by a joint motion assembly corresponds to an angle measured by a goniometer in which the fulcrum of the goniometer is aligned with the lateral epicondyle of the femur of the user, the stationary arm of the goniometer is in line in line with the greater trochanter and midline of the femur of the user, and the moving arm of the goniometer is in line with the lateral malleolus and midline of the fibula of the user.

In some embodiments, an inflection point joint angle of a flexion movement provided to a hip joint by a joint motion assembly is about 130 degrees, about 120 degrees, about 110 degrees, about 100 degrees, about 90 degrees, about 80 degrees, about 70 degrees, about 60 degrees, about 50 degrees, about 40 degrees, about 30 degrees, about 20 degrees, about 10 degrees, or about 5 degrees. In some embodiments, an inflection point joint angle of an extension movement provided to a hip joint by a joint motion assembly is about 30 degrees, about 20 degrees, about 10 degrees, or about 5 degrees. In some embodiments, an inflection point joint angle of a flexion movement or an extension movement provided to a knee joint by a joint motion assembly corresponds to an angle measured by a goniometer in which the fulcrum of the goniometer is aligned with the greater trochanter of the femur of the user, the stationary arm of the goniometer is positioned along the lateral midline of the abdomen, using the pelvis for reference, of the user, and the moving arm of the goniometer is in line with the lateral midline of the femur of the user.

In some embodiments, an inflection point joint angle of an abduction movement provided to a hip joint by a joint motion assembly is about 50 degrees, about 40 degrees, about 30 degrees, about 20 degrees, about 10 degrees, or about 5 degrees. In some embodiments, an inflection point joint angle of an adduction movement provided to a hip joint by a joint motion assembly is about 30 degrees, about 20 degrees, about 10 degrees, or about 5 degrees. In some embodiments, an inflection point joint angle of an abduction movement or an adduction movement provided to a hip joint by a joint motion assembly corresponds to an angle measured by a goniometer in which the fulcrum of the goniometer is in line with the anterior superior iliac spine of the user, the stationary arm of the goniometer is in line with the opposite anterior superior iliac spine of the user, and the moving arm of the goniometer is aligned with the midline of the patella of the user.

In some embodiments, an inflection point joint angle of a medial rotation movement provided to a hip joint by a joint motion assembly is about 50 degrees, about 40 degrees, about 30 degrees, about 20 degrees, about 10 degrees, or about 5 degrees. In some embodiments, an inflection point joint angle of lateral rotation movement provided to a hip joint by a joint motion assembly is about 40 degrees, about 30 degrees, about 20 degrees, about 10 degrees, or about 5 degrees. In some embodiments, an inflection point joint angle of a medial rotation movement or lateral rotation movement provided to a hip joint by a joint motion assembly corresponds to an angle measured by a goniometer in which the fulcrum of the goniometer is aligned with the patella of the user, the stationary arm of the goniometer is in line with the midline of the tibia of the user, and the moving arm of the goniometer is also in line with the midline of the tibia of the user.

In some embodiments, an inflection point joint angle of a flexion movement provided to a shoulder joint by a joint motion assembly is about 180 degrees, about 170 degrees, about 160 degrees, about 150 degrees, about 140 degrees, about 130 degrees, about 120 degrees, about 110 degrees, about 100 degrees, about 90 degrees, about 80 degrees, about 70 degrees, about 60 degrees, about 50 degrees, about 40 degrees, about 30 degrees, about 20 degrees, about 10 degrees, or about 5 degrees. In some embodiments, an inflection point joint angle of an extension movement provided to a shoulder joint by a joint motion assembly is about 60 degrees, about 50 degrees, about 40 degrees, about 30 degrees, about 20 degrees, about 10 degrees, or about 5 degrees. In some embodiments, an inflection point joint angle of a flexion movement or an extension movement provided to a shoulder joint by a joint motion assembly corresponds to an angle measured by a goniometer in which the fulcrum of the goniometer is placed over the acromion process of the user, the stationary arm of the goniometer is positioned in line with the midline of the humerus of the user, and the moving arm of the goniometer is in line with the lateral epicondyle of the user.

In some embodiments, an inflection point joint angle of an abduction movement provided to a shoulder joint by a joint motion assembly is about 180 degrees, about 170 degrees, about 160 degrees, about 150 degrees, about 140 degrees, about 130 degrees, about 120 degrees, about 110 degrees, about 100 degrees, about 90 degrees, about 80 degrees, about 70 degrees, about 60 degrees, about 50 degrees, about 40 degrees, about 30 degrees, about 20 degrees, about 10 degrees, or about 5 degrees. In some embodiments, an inflection point joint angle of an abduction movement provided to a shoulder joint by a joint motion assembly corresponds to an angle measured by a goniometer in which the fulcrum of the goniometer is placed at the acromion process of the user, the stationary arm of the goniometer is aligned with the anterior midline of the humerus of the user, and the moving arm of the goniometer is also aligned with the anterior midline of the humerus of the user.

In some embodiments, an inflection point joint angle of a medial rotation movement provided to a shoulder joint by a joint motion assembly is about 70 degrees, about 60 degrees, about 50 degrees, about 40 degrees, about 30 degrees, about 20 degrees, about 10 degrees, or about 5 degrees. In some embodiments, an inflection point joint angle of lateral rotation movement provided to a shoulder joint by a joint motion assembly is about 40 degrees, about 30 degrees, about 20 degrees, about 10 degrees, or about 5 degrees. In some embodiments, an inflection point joint angle of a medial rotation movement or a lateral rotation movement provided to a shoulder joint by a joint motion assembly corresponds to an angle measured by a goniometer in which the user is supine with 90 degrees of shoulder abduction and 90 degrees of elbow flexion and in which the fulcrum of the goniometer is centered over the olecranon process of the user, the stationary arm of the goniometer is aligned with the ulnar styloid the user, and the moving arm of the goniometer is perpendicular to the floor.

In some embodiments, an inflection point joint angle of a flexion movement provided to an elbow joint by a joint motion assembly is about 160 degrees, about 150 degrees, about 140 degrees, about 130 degrees, about 120 degrees, about 110 degrees, about 100 degrees, about 90 degrees, about 80 degrees, about 70 degrees, about 60 degrees, about 50 degrees, about 40 degrees, about 30 degrees, about 20 degrees, about 10 degrees, or about 5 degrees. In some embodiments, an inflection point joint angle of a flexion movement provided to an elbow joint by a joint motion assembly corresponds to an angle measured by a goniometer in which the fulcrum of the goniometer is aligned with the lateral epicondyle of the humerus of the user, the stationary arm of the goniometer is positioned along the midline of the humerus of the user, and the moving arm of the goniometer is aligned with the radial styloid process of the user.

In some embodiments, an inflection point joint angle of a supination movement provided to an elbow joint by a joint motion assembly is about 100 degrees, about 90 degrees, about 80 degrees, about 70 degrees, about 60 degrees, about 50 degrees, about 40 degrees, about 30 degrees, about 20 degrees, about 10 degrees, or about 5 degrees. In some embodiments, an inflection point joint angle of pronation movement provided to an elbow joint by a joint motion assembly is about 90 degrees, about 80 degrees, about 70 degrees, about 60 degrees, about 50 degrees, about 40 degrees, about 30 degrees, about 20 degrees, about 10 degrees, or about 5 degrees. In some embodiments, an inflection point joint angle of a supination rotation movement or a pronation rotation movement provided to an elbow joint by a joint motion assembly corresponds to an angle measured by a goniometer in which the fulcrum of the goniometer is placed just behind the ulnar styloid process of the user, the stationary arm of the goniometer is parallel with the anterior midline of the humerus of the user, and the moving arm of the goniometer parallel with the anterior midline of the humerus of the user.

In certain embodiments, an inflection point joint angle for any joint movement described herein can be calculated visually. Additional goniometer methods are known in the art, such as those described by Greene M D, Walter B, and James D. Heckman M D. The Clinical Measurement of Joint Motion. Rosemont: American Academy of Orthopaedic Surgeons, 1994 and Hislop, Helen, and Jacqueline Montgomery. Daniels and Worthingham's Muscle Testing: Techniques of Manual Examination. $6^{th}$ ed. Philadelphia: W B Saunders, 1995, the contents of each of which are hereby incorporated by reference in their entireties.

In some embodiments, an inflection point joint angle of a flexion movement of a finger metacarpophalangeal (MCP) joint provided by a joint motion assembly is about 90 degrees, about 80 degrees, about 70 degrees, about 60 degrees, about 50 degrees, about 40 degrees, about 30 degrees, about 20 degrees, about 10 degrees, or about 5 degrees. In some embodiments, an inflection point joint angle of an extension movement provided to a finger MCP joint by a joint motion assembly is about negative 20 degrees, about negative 10 degrees, about negative 5 degrees, about 0 degrees, about 5 degrees, about 10 degrees, about 20 degrees, about 30 degrees, about 40 degrees, and about 50 degrees.

In some embodiments, an inflection point joint angle of a flexion movement of a finger proximal interphalangeal (PIP) joint provided by a joint motion assembly is about 120 degrees, about 110 degrees, about 100 degrees, about 90 degrees, about 80 degrees, about 70 degrees, about 60 degrees, about 50 degrees, about 40 degrees, about 30 degrees, about 20 degrees, about 10 degrees, or about 5 degrees. In some embodiments, an inflection point joint angle of an extension movement provided to a finger PIP joint by a joint motion assembly is about negative 10 degrees, about negative 5 degrees, about 0 degrees, about 5 degrees, about 10 degrees, about 20 degrees, about 30 degrees, about 40 degrees, and about 50 degrees.

In some embodiments, an inflection point joint angle of a flexion movement of a finger distal interphalangeal (DIP) joint provided by a joint motion assembly is about 90 degrees, about 80 degrees, about 70 degrees, about 60 degrees, about 50 degrees, about 40 degrees, about 30 degrees, about 20 degrees, about 10 degrees, or about 5 degrees. In some embodiments, an inflection point joint angle of an extension movement provided to a finger DIP joint by a joint motion assembly is about negative 10 degrees, about negative 5 degrees, about 0 degrees, about 5 degrees, about 10 degrees, about 20 degrees, about 30 degrees, about 40 degrees, and about 50 degrees.

In some embodiments, an inflection point joint angle of a flexion movement of a thumb MCP joint is about 70 degrees, about 60 degrees, about 50 degrees, about 40 degrees, about 30 degrees, about 20 degrees, about 10 degrees, or about 5 degrees. In some embodiments, an inflection point joint angle of an extension movement provided to a thumb MCP joint by a joint motion assembly is about negative 10 degrees, about negative 5 degrees, about 0 degrees, about 5 degrees, about 10 degrees, about 20 degrees, about 30 degrees, about 40 degrees, and about 50 degrees.

In some embodiments, an inflection point joint angle of a flexion movement of a thumb interphalangeal joint is about 60 degrees, about 50 degrees, about 40 degrees, about 30 degrees, about 20 degrees, about 10 degrees, or about 5 degrees. In some embodiments, an inflection point joint angle of an extension movement provided to a thumb interphalangeal joint by a joint motion assembly is about negative 10 degrees, about negative 5 degrees, about 0 degrees, about 5 degrees, about 10 degrees, about 20 degrees, about 30 degrees, about 40 degrees, and about 50 degrees.

In certain embodiments, the user of the system suffers from diminished muscle function due to nerve damage resulting from, for example, a neurological defect causing paralysis, paresis, or dyscoordination. In certain embodiments, a dysfunctional muscle undergoing therapy may have diminished capacity due to nerve damage resulting from, for instance, a partially or completely severed nerve, a tumor compression or other compression of a nerve, a stroke, a transient ischemic attack, a neurodegenerative disease, e.g., ALS-Lou Gehrig's disease, Huntington's disease, multiple sclerosis, and Alzheimer's disease.

In certain embodiments, joint movement produced by an agonist muscular contraction and/or by a joint motion assembly on one side of a joint stretches antagonist muscles on the other side of the joint, which can result in motor neuron activation, muscle spindle activation, Golgi tendon organ or other mechanoreceptor activation, or combinations thereof in agonist and/or antagonist muscles and tendons thereof. In certain embodiments, stimulatory vibration of, e.g., a motor neuron, a muscle, a tendon, or a combination thereof, at frequencies of, e.g., about 30 pulses per second (pps), 40 pps, 50 pps, 60 pps, 70 pps, 80 pps, 90 pps, 100 pps, 150 pps, 200 pps, 250 pps, 500 pps, 750 pps, and 1000 pps can result in motor neuron activation, muscle spindle activation, Golgi tendon organ or other mechanoreceptor activation, or combinations thereof. Such stimulatory vibration can result in a perception of the user that a joint moved by a muscle contraction, a joint motion assembly, or a combination thereof, moves a greater amount than it actually does. In certain embodiments, stimulatory vibration of a muscle spindle, Golgi tendon organ or other mechanoreceptor, or combinations thereof, at lower frequencies of, e.g., about 25 pps, 20 pps, 15 pps, 10 pps, 5 pps, and 2 pps can result in muscle spindle activation, Golgi tendon organ or other mechanoreceptor activation, or combinations thereof. Such stimulatory vibration can result in a perception of the user that the joint moves a lesser amount than it actually does.

In certain embodiments, stimulatory vibration can be used in combination with a joint motion assembly, electrical neuromuscular stimulation, or both. In embodiments where stimulatory vibration is used in combination with a joint motion assembly, the stimulatory vibration can be applied throughout the cycle of movement provided to a joint by the joint motion assembly. The stimulatory vibration can also be applied non-continuously in cycles of movement provided to a joint of the joint motion assembly. For instance, the stimulatory vibration can be initially applied when the joint motion assembly has moved the joint a certain percentage of the range of motion the joint motion assembly moves the joint: the range of motion being defined by opposing joint movement inflection points and exemplary percentages of the range of motion at which stimulatory vibration is initially applied include about 10%, about 15%, about 20%, about 25%, about 30%, about 35%, about 40%, about 45%, about 50%, about 55%, about 60%, about 65%, about 70%, about 75%, about 80%, about 85%, about 90%, and about 95%.

The period of time for which stimulatory vibration is applied can vary, and the period can be defined by time or by a percentage of the range of motion that the joint motion assembly moves the joint. Exemplary time periods for which stimulatory vibration can be applied include about 1 ms, about 10 ms, about 100 ms, about 250 ms, about 500 ms, about 750 ms, about 1 second, about 1.25 seconds, about 1.5 seconds, about 1.75 seconds, about 2 seconds, about 3 seconds, about 5 seconds, about 10 seconds, about 15 seconds, about 20 seconds, about 25 seconds, about 30 seconds, about 35 seconds, about 40 seconds, about 45 seconds, about 50 seconds, about 50 seconds, about 55 seconds, about 1 minute, about 1.25 minutes, about 1.5 minutes, about 1.75 minutes, about 2 minutes, about 3 minutes, about 4 minutes, about 5 minutes, and 10 minutes. Exemplary percent ranges of motion for which stimulatory vibration can be applied include about 1%, about 2%, about 3%, about 4%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, and about 95%. In embodiments where stimulatory vibration is applied non-continuously in combination with a joint motion assembly providing movement to a joint, a single stimulatory vibration period or a plurality of stimulatory vibration periods can be used in the cycle of movement provided to the joint by the joint motion assembly. In certain embodiments, stimulatory vibration can be applied when a joint is at a point, in a cycle of movement provided by joint motion assembly, at which the joint is not a motion, e.g., a joint movement inflection point in the cycle or a stop point in the cycle.

In certain embodiments, electrical neuromuscular stimulation can be used in combination with a joint motion assembly, stimulatory vibration, or both. In embodiments where electrical neuromuscular stimulation is used in combination with a joint motion assembly, the stimulatory electrical energy can be applied throughout the cycle of movement provided to a joint by the joint motion assembly. The stimulatory electrical energy can also be applied non-continuously in cycles of movement provided to a joint of the joint motion assembly. For instance, the stimulatory electrical energy can be initially applied when the joint motion assembly has moved the joint a certain percentage of the range of motion the joint motion assembly moves the joint: the range of motion being defined by opposing joint movement inflection points and exemplary percentages of the range of motion at which stimulatory vibration is initially applied include about 10%, about 15%, about 20%, about 25%, about 30%, about 35%, about 40%, about 45%, about 50%, about 55%, about 60%, about 65%, about 70%, about 75%, about 80%, about 85%, about 90%, and about 95%. The period of time for which stimulatory electrical energy is applied can vary, and the period can be defined by time or by a percentage of the range of motion that the joint motion assembly moves the joint. Exemplary time periods for which stimulatory electrical energy can be applied include about 1 millisecond (ms), about 10 ms, about 100 ms, about 250 ms, about 500 ms, about 750 ms, about 1 second, about 1.25 seconds, about 1.5 seconds, about 1.75 seconds, about 2 seconds, about 3 seconds, about 5 seconds, about 10 seconds, about 15 seconds, about 20 seconds, about 25 seconds, about 30 seconds, about 35 seconds, about 40 seconds, about 45 seconds, about 50 seconds, about 50 seconds, about 55 seconds, and about 1 minute. Exemplary percent ranges of motion for which stimulatory electrical energy can be applied include about 1%, about 2%, about 3%, about 4%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, and about 95%. In embodiments where stimulatory electrical energy is applied non-continuously in combination with a joint motion assembly providing movement to a joint, a single stimulatory vibration period or a plurality of stimulatory vibration periods can be used in the cycle of movement provided to the joint by the joint motion assembly. In certain embodiments, stimulatory electrical energy can be applied when a joint is at a point, in a cycle of movement provided by joint motion assembly, at which the joint is not a motion, e.g., a joint movement inflection point in the cycle or a stop point in the cycle.

In certain embodiments, stimulatory vibration and stimulatory electrical energy can both be applied in the course of a cycle of movement provided to a joint by a joint motion assembly. In embodiments where stimulatory vibration and stimulatory electrical energy are applied in the course of a cycle of movement provided by a joint motion assembly, the points and periods in which the stimulatory vibration in the stimulatory electrical energy are applied can be the same or different and can be discrete or overlapping.

What is claimed is:

1. An apparatus, for treating diminished muscle function in an upper extremity, comprising:
    an electrical member that delivers electrical energy to a hand region comprising at least one of a digit, a hand, and a wrist, the hand region comprising a dysfunctional muscle;
    a hand joint motion assembly that couples to the hand region and provides, by an electric motor, a joint motion, in a cycle comprising opposing joint movements, to a joint, at a junction of two bones forming an angle for which the junction is the vertex, to which the dysfunctional muscle ordinarily provides motion; and
    that controls (i) a timing of electrical energy delivery by the member and (ii) an amount of electrical energy delivered by the member;
    wherein the angle is at a minimum at maximal flexion of the joint and is at a maximum at maximal extension of the joint;
    wherein the timing of electrical energy delivery is controlled to occur only while both of the following occur simultaneously: (i) the angle is within about 30 degrees of at least one of the minimum and maximum, and (ii) motion is being provided to the joint by the joint motion assembly; and
    wherein the amount of electrical energy delivered is effective to result in a depolarization of at least one of the dysfunctional muscle and a nerve that innervates the dysfunctional muscle.

2. The system of claim 1, wherein the depolarization results in a contraction of the dysfunctional muscle.

3. The system of claim 2, wherein the contraction results in a force on the joint that is antagonistic toward the joint movement being provided by the joint motion assembly at the time of contraction.

4. The system of claim 2, wherein the contraction results in a force on the joint that is protagonistic toward the joint motion being provided by the joint motion assembly at the time of contraction.

5. The system of claim 1, wherein the member delivers the electrical energy when the angle is within about 20 degrees of the at least one of the minimum and maximum.

6. The system of claim 1, wherein the member delivers the electrical energy when the angle is within about 15 degrees of the at least one of the minimum and maximum.

7. The system of claim 1, wherein the member delivers the electrical energy when the angle is within about 10 degrees of the at least one of the minimum and maximum.

8. The system of claim 1, wherein the member delivers the electrical energy when the angle is within about 5 degrees of the at least one of the minimum and maximum.

9. The system of claim 1, further comprising a vibratory member, in communication with the assembly, that delivers vibratory energy to at least one of the digit, the hand, and the wrist effective to result in activation of a mechanoreceptor in proximity to the joint.

10. A method, for treating diminished muscle function in an upper extremity, comprising:
    contacting an electrical member, configured to deliver electrical energy, to a hand region comprising at least one of a digit, a hand, and a wrist, the hand region comprising a dysfunctional muscle;
    with an electric motor of a joint motion assembly, providing a joint motion, in a cycle comprising opposing joint movements, to a joint of the hand region, at a junction of two bones forming angle for which the junction is the vertex, to which the dysfunctional muscle ordinarily provides movement;
    wherein the angle is at a minimum at maximal flexion of the joint and is at a maximum at maximal extension of the joint; and
    with the electrical member, delivering an amount of electrical energy to the hand region only while both of the following occur simultaneously: (i) the angle is positioned within about 30 degrees of at least one of the minimum and maximum, and (ii) the joint motion is being provided to the joint;
    wherein the amount of electrical energy delivered is effective to result in a depolarization, in the hand region, of at least one of the dysfunctional muscle and a nerve that innervates the dysfunctional muscle.

11. The method of claim 10, wherein the depolarization results in a contraction the dysfunctional muscle.

12. The method of claim 11, wherein the contraction results in a force on the joint that is antagonistic toward the joint movement being provided by the joint motion assembly at the time of contraction.

13. The method of claim 11, wherein the contraction results in a force on the joint that is protagonistic toward the joint movement being provided by the joint motion assembly at the time of contraction.

14. The method of claim 10, wherein the delivery of electrical energy occurs when the an is within about 20 degrees of the at least one of the minimum and maximum.

15. The method of claim 10, wherein the delivery of electrical energy occurs when the angle is within 15 degrees of the at least one of the minimum and maximum.

16. The method of claim 10, wherein the delivery of electrical energy occurs when the angle is within 10 degrees of the at least one of the minimum and maximum.

17. The method of claim 10, wherein the delivery of electrical energy occurs when the an is within 5 degrees of the at least one of the minimum and maximum.

* * * * *